(12) United States Patent
Kim et al.

(10) Patent No.: US 11,096,433 B2
(45) Date of Patent: Aug. 24, 2021

(54) TROUSERS WITH WAIST PROTECTION BELT

(71) Applicant: MIDORI ANZEN CO., LTD., Tokyo (JP)

(72) Inventors: Jaewoo Kim, Tokyo (JP); Naotoshi Matsubayashi, Tokyo (JP); Shohei Tamanaha, Tokyo (JP); Kagari Sako, Tokyo (JP)

(73) Assignee: MIDORI ANZEN CO., LTD., Tokyo (JP)

( * ) Notice: Subject to any disclaimer, the term of this patent is extended or adjusted under 35 U.S.C. 154(b) by 0 days.

(21) Appl. No.: 15/770,335

(22) PCT Filed: Jun. 6, 2016

(86) PCT No.: PCT/JP2016/066714
§ 371 (c)(1),
(2) Date: Apr. 23, 2018

(87) PCT Pub. No.: WO2017/073105
PCT Pub. Date: May 4, 2017

(65) Prior Publication Data
US 2018/0310646 A1 Nov. 1, 2018

(30) Foreign Application Priority Data
Oct. 27, 2015 (JP) .............................. JP2015-211314

(51) Int. Cl.
*A41D 13/05* (2006.01)
*A41D 1/06* (2006.01)
(Continued)

(52) U.S. Cl.
CPC ........... *A41D 13/0525* (2013.01); *A41D 1/06* (2013.01); *A41D 1/14* (2013.01); *A41D 13/05* (2013.01);
(Continued)

(58) Field of Classification Search
CPC ............ A41B 2300/30; A41D 2300/30; A41D 2200/10; A41D 1/06; A45F 5/021; A61F 5/026
(Continued)

(56) References Cited

U.S. PATENT DOCUMENTS 4,890,337 A * 1/1990 Greenberg ............... A41D 1/06
2/220
5,188,586 A * 2/1993 Castel ..................... A61F 5/028
128/845

(Continued)

FOREIGN PATENT DOCUMENTS

CN 201742955 U 2/2011
CN 202536149 U 11/2012
(Continued)

OTHER PUBLICATIONS

The extended European search report issued by the European Patent Office dated Feb. 19, 2020, which corresponds to European Patent Application No. 16859342.4-1122 and is related to U.S. Appl. No. 15/770,335.
(Continued)

*Primary Examiner* — Jillian K Pierorazio
(74) *Attorney, Agent, or Firm* — Studebaker & Brackett PC

(57) ABSTRACT

This disclosure is related to trousers with a waist protection belt. The trousers include the waist protection belt that is detachably attached to a belt cloth of the trousers, a trouser body that includes a stretchable cloth at a position corresponding to a waist part of a back body part of the trousers, and a position adjusting part that is provided at substantially a center of the waist protection belt and is provided at a position on a back surface of the belt cloth corresponding to the waist part of the trouser body. The position adjusting part is configured to adjustably change an attachment position of
(Continued)

the waist protection belt in a vertical direction with respect to the trouser body.

11 Claims, 20 Drawing Sheets

(51) Int. Cl.
*A41D 1/14* (2006.01)
*A41D 27/12* (2006.01)
*A61F 5/02* (2006.01)
*A41F 9/00* (2006.01)
*A61F 5/03* (2006.01)

(52) U.S. Cl.
CPC .............. *A41D 27/12* (2013.01); *A41F 9/002* (2013.01); *A61F 5/02* (2013.01); *A61F 5/028* (2013.01); *A61F 5/03* (2013.01); *A41D 2200/10* (2013.01); *A41D 2300/32* (2013.01); *A41D 2400/32* (2013.01); *A41D 2600/20* (2013.01)

(58) Field of Classification Search
USPC .......................................... 602/19; 2/44, 45
See application file for complete search history.

(56) References Cited

U.S. PATENT DOCUMENTS

| | | | | |
|---|---|---|---|---|
| 5,257,419 | A * | 11/1993 | Alexander | A61F 5/028 2/338 |
| 5,334,134 | A * | 8/1994 | Saunders | A41D 13/0525 128/100.1 |
| 5,471,680 | A * | 12/1995 | Vesterinen | A41D 13/0525 2/338 |
| 6,108,819 | A * | 8/2000 | DeBaene | A41D 1/067 2/227 |
| 6,311,333 | B1 * | 11/2001 | Batra | A41D 1/06 2/221 |
| D626,244 | S * | 10/2010 | Sagnip | D24/190 |
| 2002/0092084 | A1 * | 7/2002 | Takayama | A41F 9/00 2/236 |
| 2005/0229295 | A1 * | 10/2005 | Chun | A41D 13/0506 2/467 |
| 2011/0172577 | A1 * | 7/2011 | Arsenault | A61F 5/028 602/19 |
| 2017/0303604 | A1 | 10/2017 | Kasabo et al. | |

FOREIGN PATENT DOCUMENTS

| | | |
|---|---|---|
| CN | 204466971 U | 7/2015 |
| CN | 106793839 A | 5/2017 |
| EP | 3207813 A1 | 8/2017 |
| GB | 2259848 A | 3/1993 |
| JP | S62-157519 U | 10/1987 |
| JP | H06-006812 Y | 2/1994 |
| JP | H07-503647 A | 4/1995 |
| JP | H08-089520 A | 4/1996 |
| JP | 3030834 U | 11/1996 |
| JP | H10-046409 A | 2/1998 |
| JP | 3052914 U | 10/1998 |
| JP | 2001-181903 A | 7/2001 |
| JP | 2006-063485 A | 3/2006 |
| JP | 2008-081864 A | 4/2008 |
| JP | 2009-114553 A | 5/2009 |
| JP | 2011-130974 A | 7/2011 |
| JP | 3172676 U | 1/2012 |
| JP | 2012-233292 A | 11/2012 |
| JP | 2014-113434 A | 6/2014 |
| JP | 2014-132132 A | 7/2014 |
| JP | 3199495 U | 8/2015 |
| WO | 2011/019332 A1 | 2/2011 |
| WO | 2016/060152 A1 | 4/2016 |

OTHER PUBLICATIONS

An Office Action mailed by the Japanese Patent Office dated Nov. 6, 2018, which corresponds to Japanese Patent Application No. 2017-547640 and is related to U.S. Appl. No. 15/770,335.

An Office Action mailed by the State Intellectual Property Office of the People's Republic of China dated Dec. 23, 2019, which corresponds to Chinese Patent Application No. 201680051909.7 and is related to U.S. Appl. No. 15/770,335.

An Office Action; "Notification of Reasons for Refusal," issued by the Japanese Patent Office dated Aug. 21, 2018, which corresponds to Japanese Patent Application No. 2017-547640 and is related to U.S. Appl. No. 15/770,335; with English language translation.

International Search Report; issued in PCT/JP2016/066714; dated Jul. 12, 2016.

An Office Action issued by the China National Intellectual Property Administration dated Sep. 3, 2020, which corresponds to Chinese Patent Application No. 201680051909.7 and is related to U.S. Appl. No. 15/770,335 with English language translation.

An Office Action; "Notice of Reasons for Refusal," mailed by the Japanese Patent Office dated Oct. 6, 2020, which corresponds to Japanese Patent Application No. 2019-000822 and is related to U.S. Appl. No. 15/770,335; with English language translation.

* cited by examiner

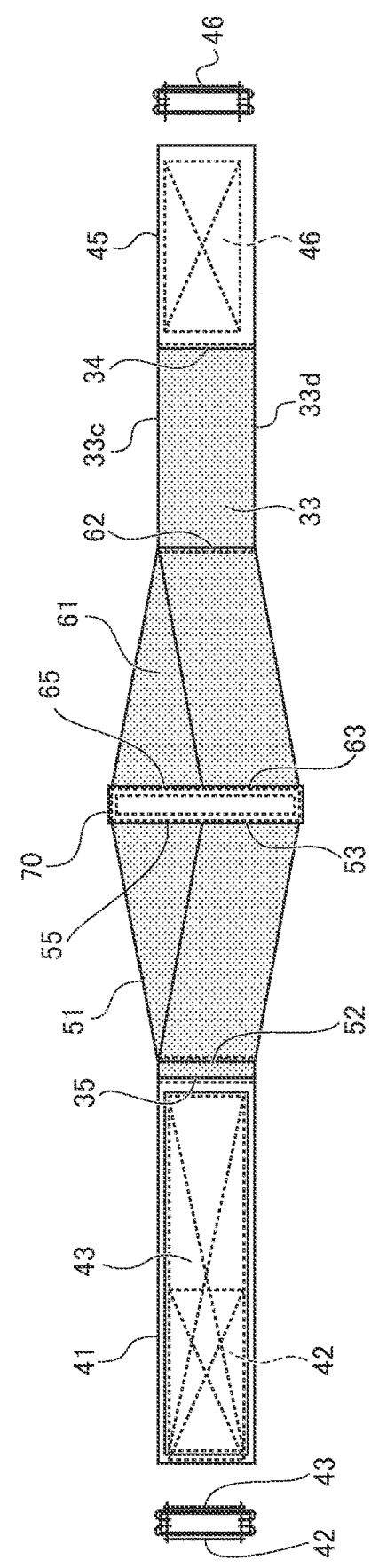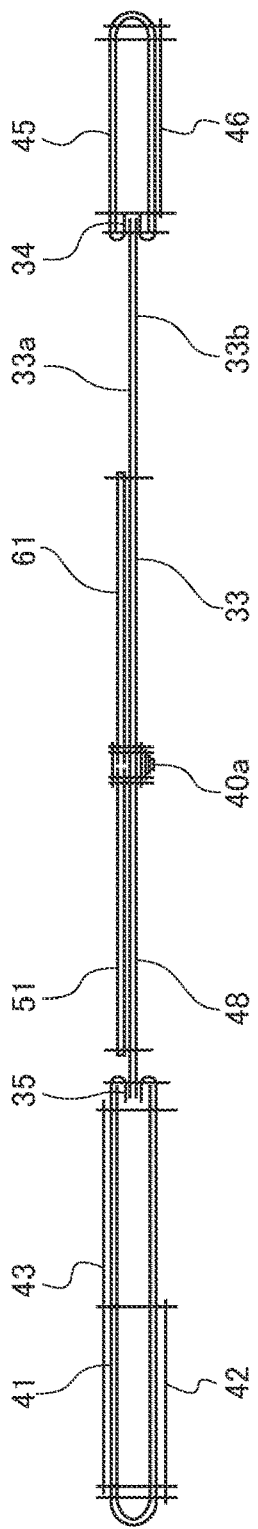

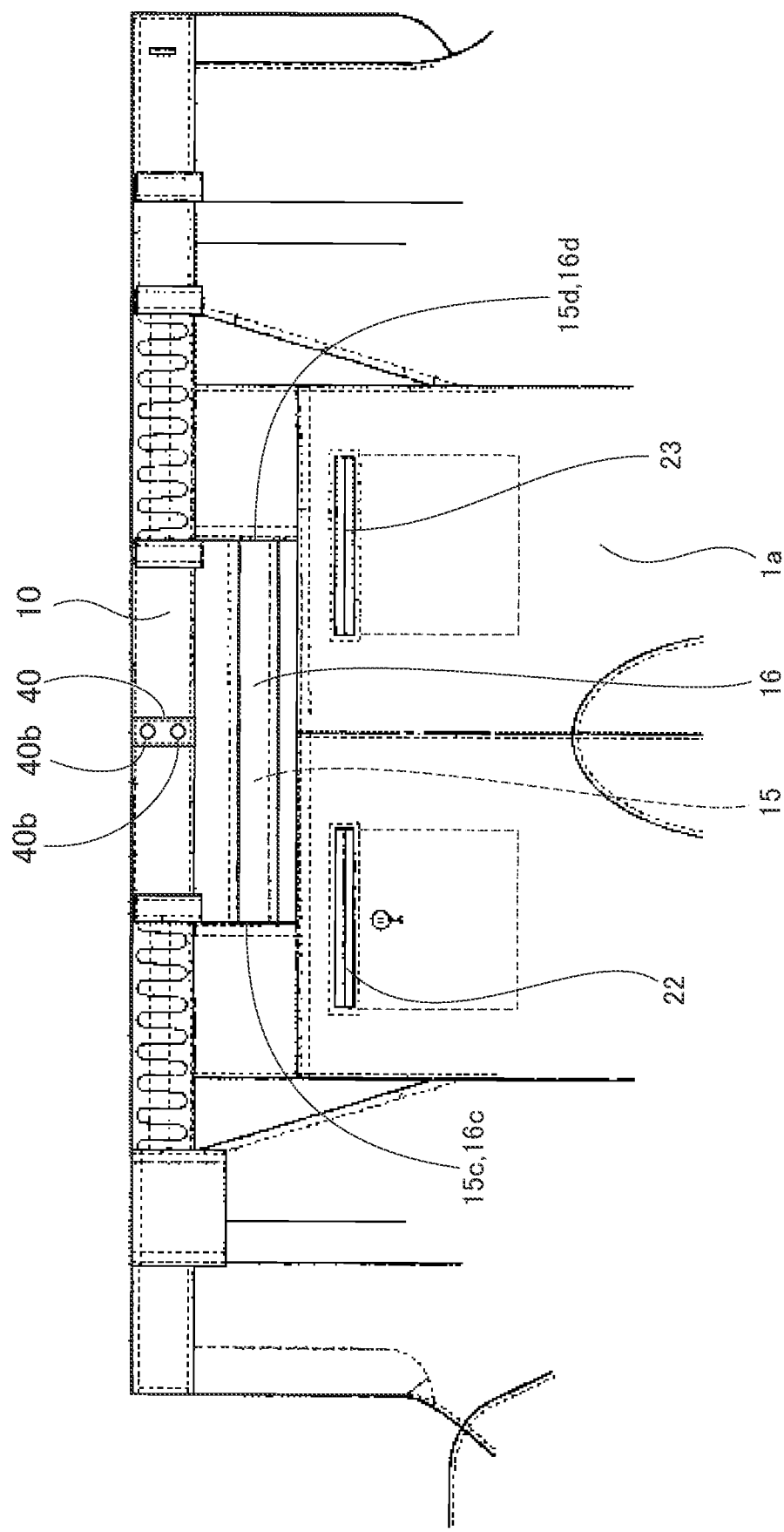

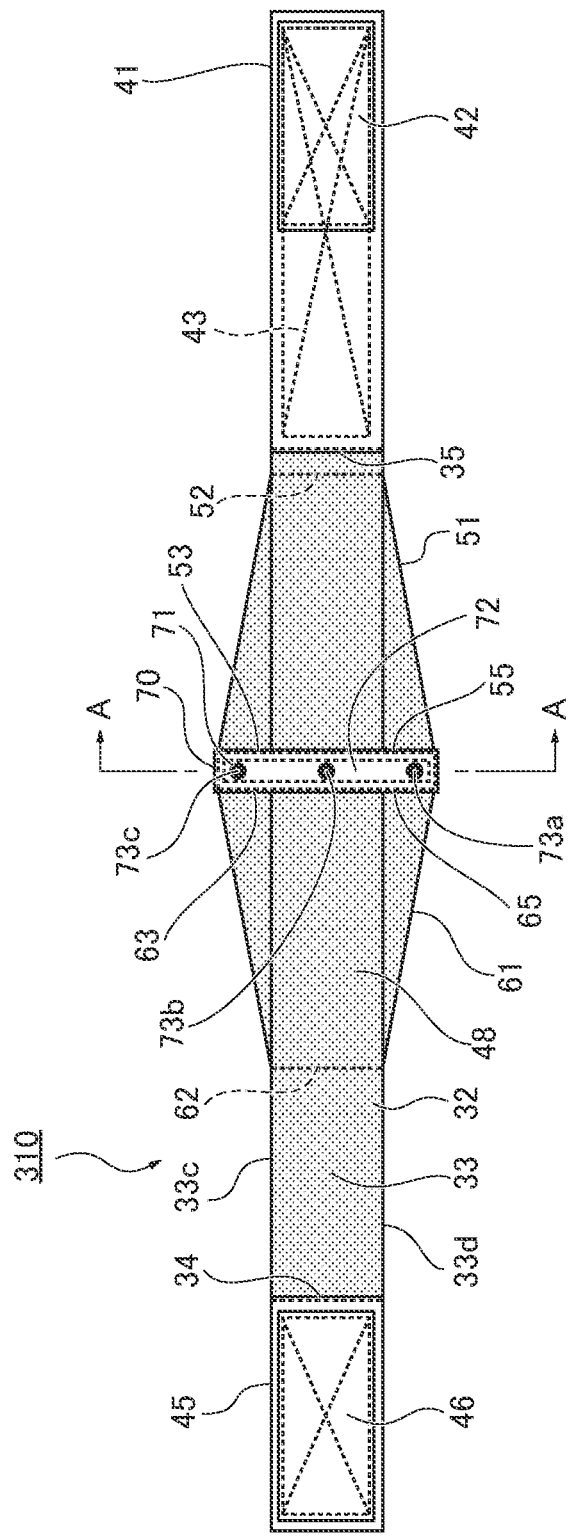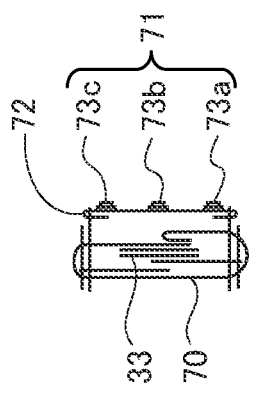
FIG.16A
FIG.16B

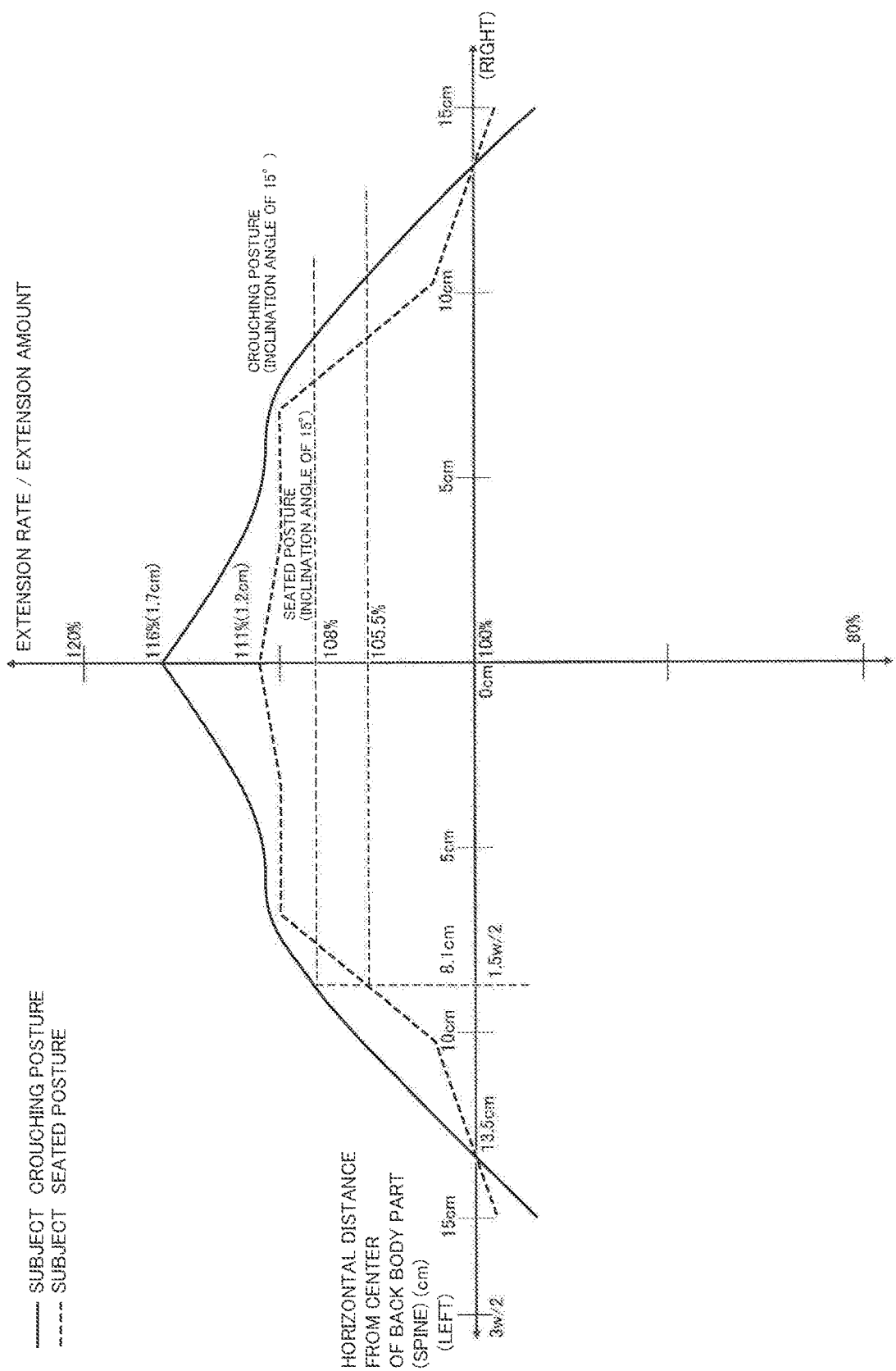

| TROUSERS NORMAL | SUBJECT A | | | | | | |
|---|---|---|---|---|---|---|---|
| POSITION | POINT BELOW LEFT SCAPULA (P1) | POINT BELOW LEFT AXILLARY (P2) | POINT BELOW LEFT NIPPLE (P3) | POINT ON MEDIAL LINE (P4) | POINT BELOW RIGHT NIPPLE (P5) | POINT BELOW RIGHT AXILLARY (P6) | POINT BELOW RIGHT SCAPULA (P7) |
| STANDING | 0.04 | 1.20 | 1.07 | 1.08 | 0.69 | 1.10 | 0.63 |
| KNEELING | 0.03 | 3.38 | 2.62 | 2.33 | 1.84 | 1.38 | 0.09 |
| SEATED | 0.78 | 2.05 | 1.12 | 1.75 | 1.41 | 1.30 | 0.15 |

(II)

| TROUSERS 1a | SUBJECT A | | | | | | |
|---|---|---|---|---|---|---|---|
| POSITION | POINT BELOW LEFT SCAPULA (P1) | POINT BELOW LEFT AXILLARY (P2) | POINT BELOW LEFT NIPPLE (P3) | POINT ON MEDIAL LINE (P4) | POINT BELOW RIGHT NIPPLE (P5) | POINT BELOW RIGHT AXILLARY (P6) | POINT BELOW RIGHT SCAPULA (P7) |
| KNEELING | 0.06 | 1.78 | 0.87 | 0.81 | 0.70 | 0.81 | 0.15 |
| SEATED | 0.07 | 1.70 | 0.97 | 1.39 | 1.03 | 0.87 | 0.25 |

(III)

| TROUSERS NORMAL | SUBJECT B | | | | | | |
|---|---|---|---|---|---|---|---|
| POSITION | POINT BELOW LEFT SCAPULA (P1) | POINT BELOW LEFT AXILLARY (P2) | POINT BELOW LEFT NIPPLE (P3) | POINT ON MEDIAL LINE (P4) | POINT BELOW RIGHT NIPPLE (P5) | POINT BELOW RIGHT AXILLARY (P6) | POINT BELOW RIGHT SCAPULA (P7) |
| STANDING | 1.54 | 3.35 | 1.95 | 1.80 | 2.50 | 3.60 | 2.42 |
| KNEELING | 0.47 | 5.04 | 4.90 | 3.86 | 4.13 | 4.51 | 0.22 |
| SEATED | 0.41 | 3.35 | 2.41 | 2.91 | 3.05 | 3.41 | 0.54 |

(IV)

| TROUSERS 1a | SUBJECT B | | | | | | |
|---|---|---|---|---|---|---|---|
| POSITION | POINT BELOW LEFT SCAPULA (P1) | POINT BELOW LEFT AXILLARY (P2) | POINT BELOW LEFT NIPPLE (P3) | POINT ON MEDIAL LINE (P4) | POINT BELOW RIGHT NIPPLE (P5) | POINT BELOW RIGHT AXILLARY (P6) | POINT BELOW RIGHT SCAPULA (P7) |
| STANDING | 1.30 | 3.14 | 1.61 | 1.09 | 1.69 | 3.27 | 1.86 |
| KNEELING | 0.71 | 2.83 | 2.09 | 1.64 | 1.89 | 2.49 | 0.52 |
| SEATED | 1.00 | 2.67 | 1.61 | 1.48 | 1.77 | 2.69 | 1.74 |

UNIT (kPa)   *ERROR ±0.1kPa

POINT ON MEDIAL LINE (P4)
POINT DIRECTLY BELOW LEFT NIPPLE (P3)
POINT DIRECTLY BELOW LEFT AXILLARY (P2)
POINT DIRECTLY BELOW RIGHT AXILLARY (P6)
POINT DIRECTLY BELOW RIGHT NIPPLE (P5)

FRONT

POINT DIRECTLY BELOW LEFT SCAPULA (P1)
POINT DIRECTLY BELOW RIGHT SCAPULA (P7)

BACK

TROUSERS WITH WAIST PROTECTION BELT

CROSS-REFERENCE TO RELATED APPLICATION

The present application is based on and claims priority to Japanese Patent Application No. 2015-211314, filed on Oct. 27, 2015, the disclosure of which is hereby incorporated by reference in its entirety.

TECHNICAL FIELD

This invention relates to trousers with a waist protection belt attached to a belt part of the trousers.

BACKGROUND ART

JPH06-006812 Y2 (Patent Literature (PLT) 1) teaches a waist protection belt which is used by a worker while working. The waist protection belt of the PLT 1 comprises a waist-back part and abdomen parts. The waist-back part and the abdomen parts each includes an elastic core material, and supports and holds the pelvic of the worker (i.e., wearer) with a predetermined width (e.g., 10 to 15 cm). With the waist protection belt, the pelvic of the worker is firmly fixed to reduce pressure at the lumber vertebrae and to prevent positional displacement of the lumbosacral joint.

Additionally, JP2008-081864 A (Patent Literatures 2) and JPH10-046409 A (Patent Literature 3) each teaches trousers with a waist protection belt. In order to prevent the position of the waist protection belt from moving with respect to the trousers, the waist protection belt of the PLTs 2 and 3 are connected and fixed to the trousers. As the trousers and the waist protection belt are integrally provided, the wearer can easily adjust the position and/or the tightness of the waist protection belt without taking off the trousers. Accordingly, the PLTs 2 and 3 provide a technique to improve the convenience at the work when the worker uses a waist protection belt.

SUMMARY

Technical Problem

The techniques in PLTs 2 and 3 allow the wearer to fix the relative position between the waist protection belt and the trousers. However, since the trousers are designed and manufactured based on the standing posture, the relative positions of the belt to the trousers differ between the standing posture and the seated posture. That is, when the wearer changes his posture from the standing posture to the seated posture, the position of the waist protection belt moves and thereby it is unable to keep the waist protection belt at the suitable and desirable position.

Further, it is preferable to use the waist protection belt to cover around the pelvic of the wearer. However, the position of the pelvic may differ depending on each of the wearers. Therefore, it is desirable to provide a waist protection belt which the wearer is able to adjust the wearing position thereof.

Solution to Problem

In order to achieve the above object, trousers with a waist protection belt in accordance with an embodiment of this disclosure are configured to include a trouser body, a stretchable cloth provided at a position corresponding to a waist part of the trouser body, and a waist protection belt attached to a belt cloth of the trouser body.

Further, trousers with a waist protection belt in accordance with another embodiment of this disclosure are configured to include a waist protection belt detachably attached to a belt cloth of the trousers, a trouser body including a stretchable cloth at a waist part of a back body part of the trousers, and a position adjusting part that is provided at a substantially center part of the waist protection belt and is provided at a position on a back surface of the belt cloth at the waist part of the trouser body. The position adjusting part is configured to adjustably change an attachment position of the waist protection belt in a vertical direction with respect to the trouser body.

BRIEF DESCRIPTION OF DRAWINGS

FIG. 13A is a back view illustrating the waist protection belt according to the First Embodiment of this disclosure.

FIG. 13B is a left side view illustrating the waist protection belt according to the First Embodiment of this disclosure.

FIG. 13C is a right side view illustrating the waist protection belt according to the First Embodiment of this disclosure.

FIG. 13D is a plan view illustrating the waist protection belt according to the First Embodiment of this disclosure.

FIG. 15 is a back view illustrating another example of the trousers according to the First Embodiment of this disclosure.

FIG. 16A is a front view illustrating a waist protection belt according to a Second Embodiment of this disclosure.

FIG. 16B is a right side view illustrating a waist protection belt according to the Second Embodiment of this disclosure.

FIG. 20 is a first reference material showing extension amounts of the back body part in a crouching posture and in a seated posture.

FIG. 21 is a second reference material showing measurement results of clothing pressures.

FIG. 22A is a third reference material showing measuring points for the clothing pressures shown in FIG. 21.

FIG. 22B is the third reference material showing the measuring points for the clothing pressures shown in FIG. 21.

DESCRIPTION OF EMBODIMENTS

Figure 1:
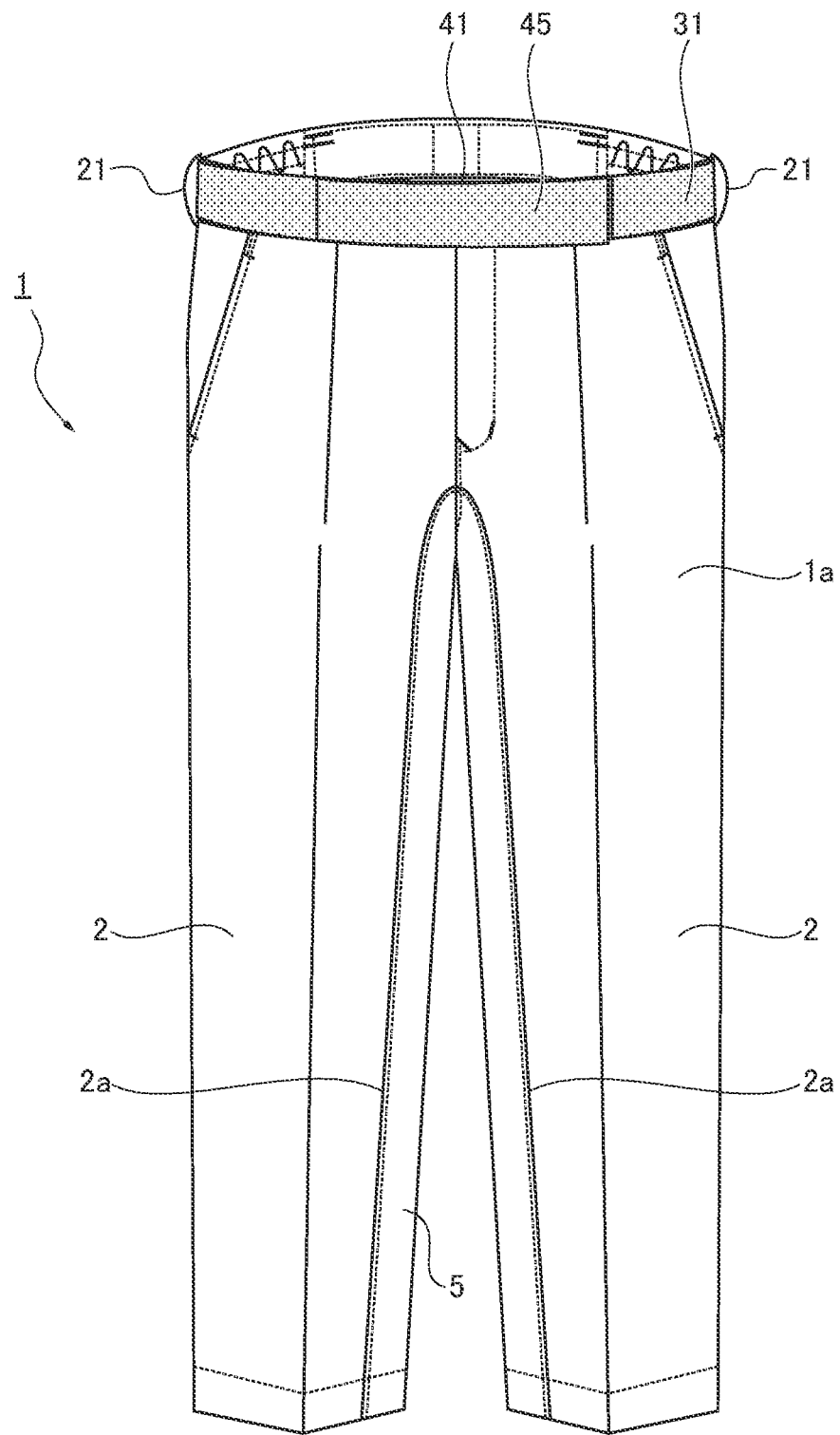
FIG. 1 is a front view illustrating trousers with a waist protection belt according to a First Embodiment of this disclosure.

Hereinafter, embodiments of trousers with a waist protection belt will be described with reference to the drawings attached hereto.

First Embodiment

As illustrated in FIGS. 1-5, trousers 1 with a waist protection belt according to a First Embodiment of this disclosure includes a trouser body 1a of the trousers 1, a stretchable cloth 15, a cover cloth 16 which covers the stretchable cloth 15, and a waist protection belt 31.

The stretchable cloth 15 is provided at a position corresponding to the waist part of the trouser body 1. In the trouser body 1a, an inner edge 2a of the crotch portion of a front body part 2 is sewn to an inner edge 3a of the crotch portion of a back body part 3, an outer edge 2b of the crotch portion of the front body part 2 is sewn to an outer edge 3b of the crotch portion of the back body part 3, and a belt cloth 10 is sewn to an upper edge 2d of the front body part 2 and an upper edge 3d of the back body part 3.

Figure 6:
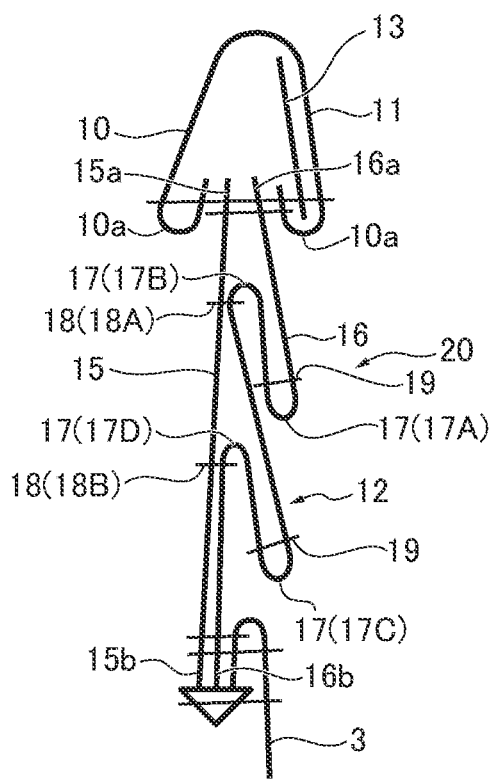
FIG. 6 is a schematic view illustrating an enlarged cross section of a stretchable cloth formed on the trousers according to the First Embodiment of this disclosure.

As illustrated in FIG. 6, the trouser body 1a is formed with an annular-shaped belt part 11.

The belt part 11 is formed by folding the band-shaped belt cloth 10 in half, by wrapping or sandwiching the upper edge 2d of the front body part 2 and the upper edge part 3d of the back body part 3 by folded edges 10a, 10a of the belt cloth 10 respectively, and then by sewing the upper edge parts 2d, 3d of the front body part 2 and the back body part 3 with the folded edges 10a, 10a of the belt cloth 10. The front body part 2, the back body part 3, and the belt cloth 10 are made of a cloth having little stretchability.

As illustrated in FIGS. 1 to 5, the trouser body 1a of the trousers 1 may include, in addition to the pair of the left and right front body parts 2 and the pair of the right and left back body parts 3, a gusset part 5 sewn to the front body parts 2 and the back body parts 3 at the inner crotch side thereof. The gusset part 5 is continuously formed between the bottom of a right leg portion 6 and the bottom of a left leg portion 7, and sewn to the inner edge 2a of the front body part 2 and to the inner edge 3a of the back body part 3 (see FIG. 7, for example). In this disclosure, the left and right are defined based on the view of the wearer of the trousers 1 unless otherwise specified. Further, in FIGS. 2 and 5, the left side on the papers is the front side F, and the right side on the papers is the rear side R.

Figure 7:
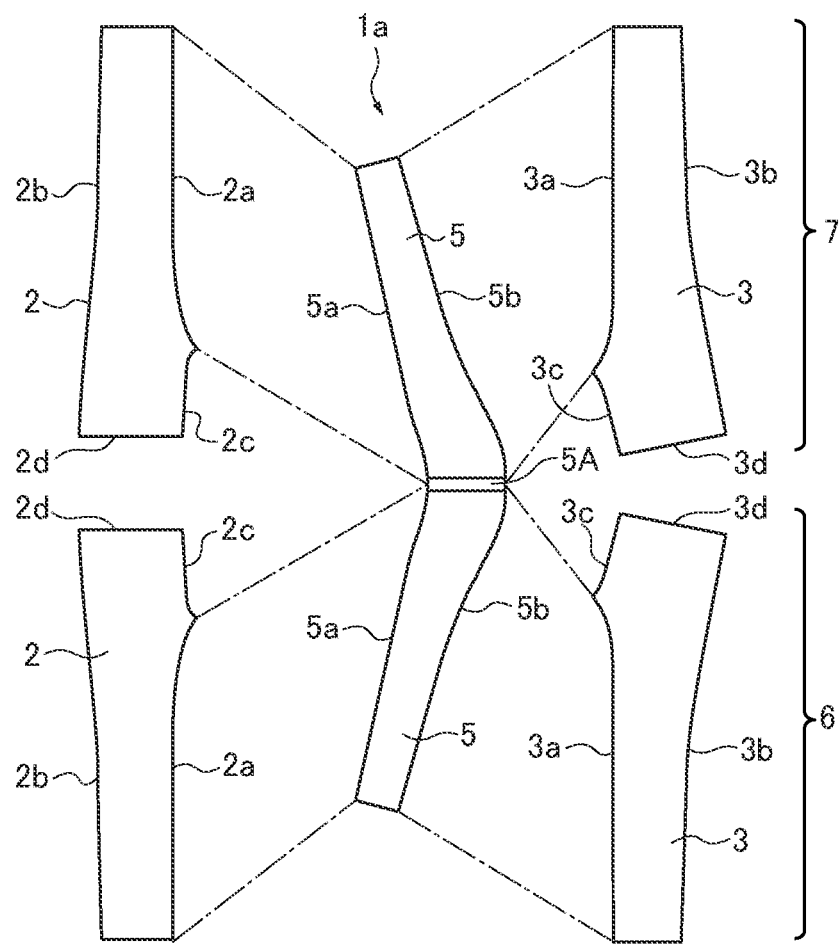
FIG. 7 is a plan view illustrating front body parts, back body parts, and gusset parts of the trousers according to the First Embodiment of this disclosure.

As illustrated in FIG. 7, the gusset part 5 is a single cut part. The trousers body 1a is manufactured by sewing the cut front body parts 2, 2 and the cut back body parts 3, 3 with the gusset part 5. Specifically, the trouser body 1a is manufactured by respectively sewing the inner edges 2a of the front body part 2 and front edges 5a of the gusset part 5 on the left and right sides, by respectively sewing the inner edges 3a of the back body part 3 and rear edges 5b of the gusset part 5 on the left and right sides, by respectively sewing the outer edges 2b of the front body part 2 and the outer edges 3b of the back body part 3, by sewing body-side edges 2c, 2c of the front body part 2 to each other through a zip fastener (not illustrated), and by sewing body-side edges 3c, 3c of the back body part 3 to each other.

When the trouser body 1a of the First Embodiment is provided with the above-described gusset part 5, the movable range of the leg parts of the trouser body 1a expands. That is, the wearer of the trousers 1 can easily take a crouching posture, for example. Accordingly, it is possible to avoid unnecessary load on the wearer's waist.

Figure 4:
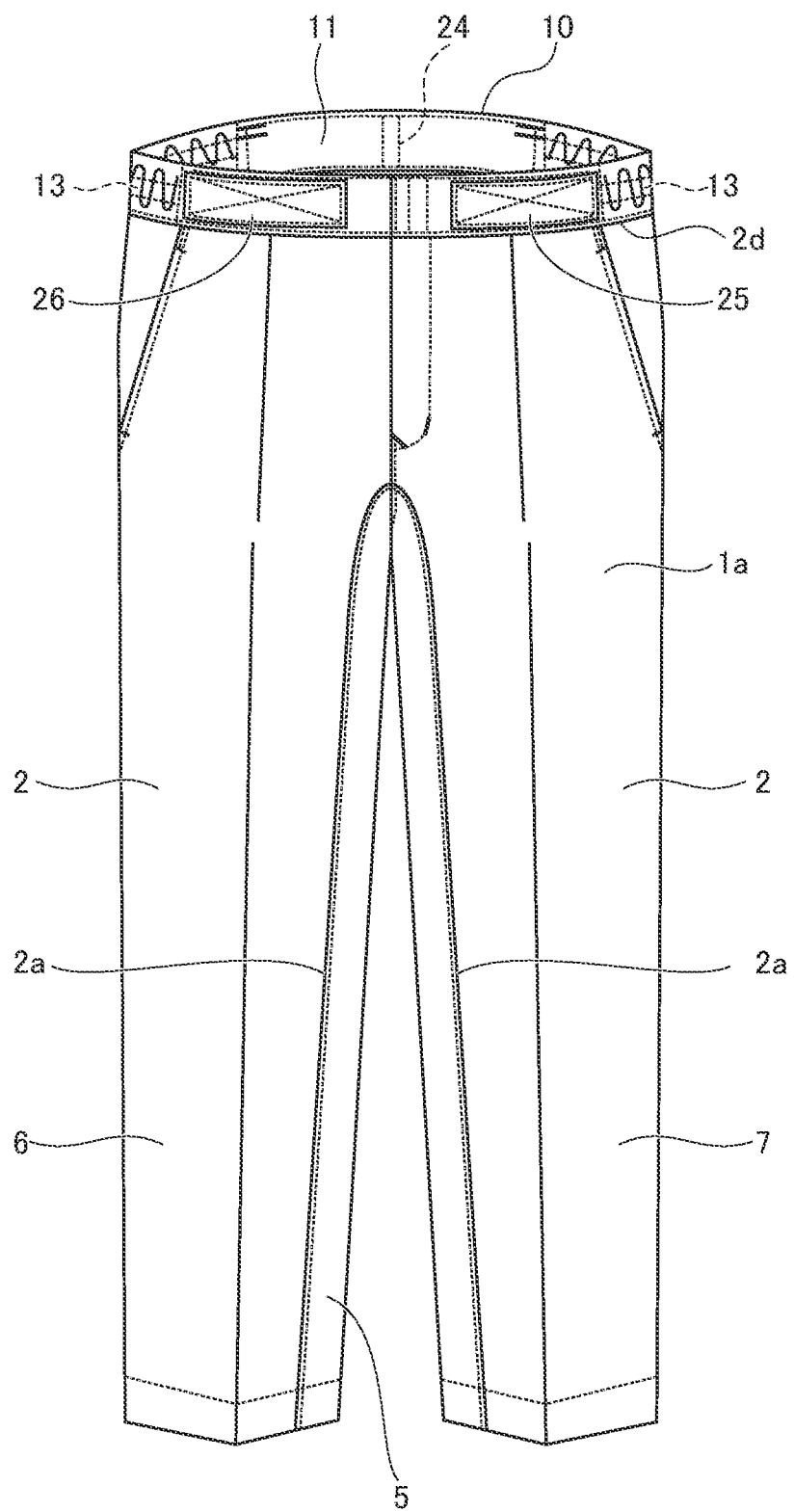
FIG. 4 is a front view illustrating the trousers without the waist protection belt according to the First Embodiment of this disclosure.

Additionally, as illustrated in FIG. 4, the trouser body 1a is provided with elastic members 13 at some areas on the annular-shaped belt part 11 in the longitudinal direction (i.e., direction of waistline). To be specific, the elastic members 13 are provided at the areas corresponding to the left and right sides of the wearer's waist such that the trouser body 1a is configured to be stretchable. The elastic members 13 are made of, for example, rubber strings and are provided inside the cylindrical belt cloth 10 (see FIG. 8).

Figure 5:
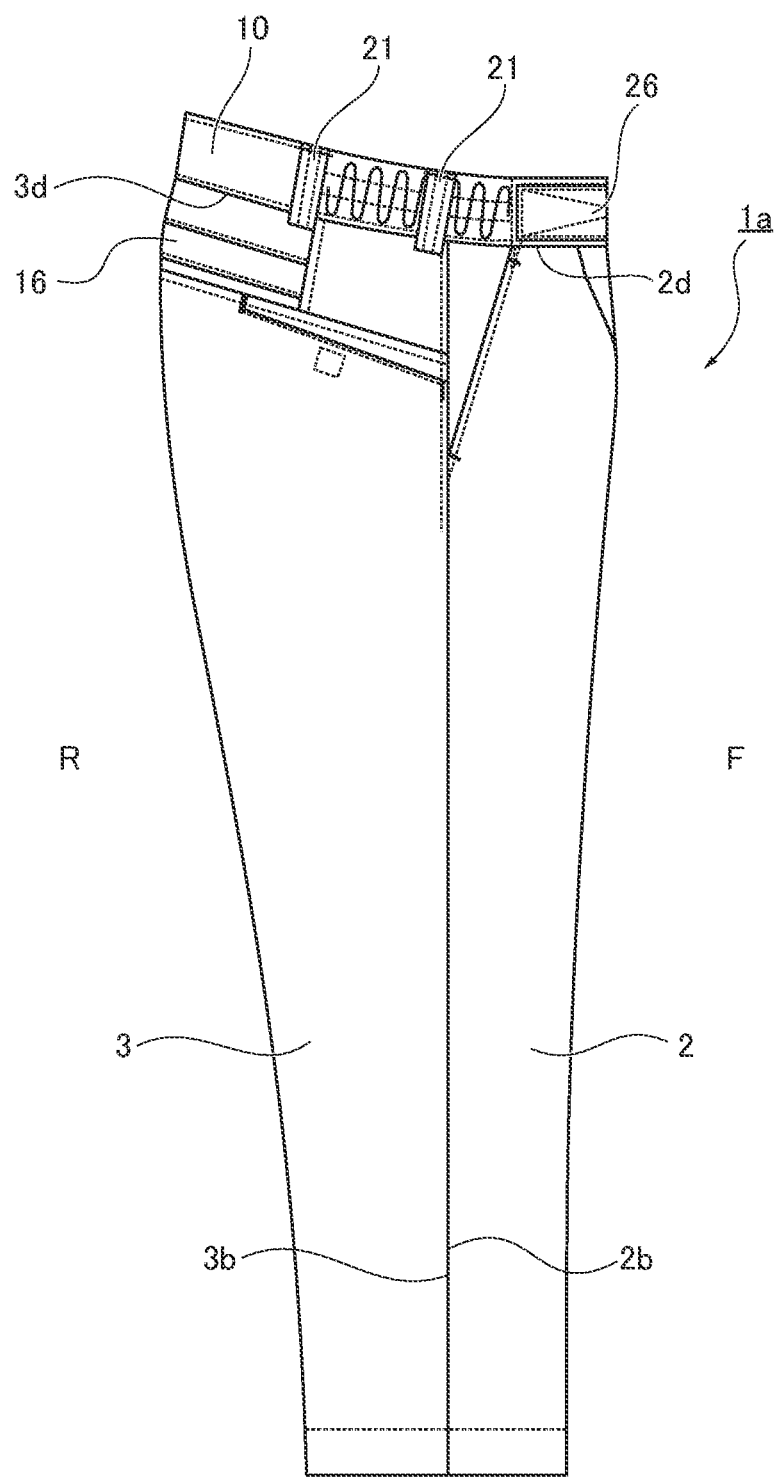
FIG. 5 is a left side view illustrating the trousers without the waist protection belt according to the First Embodiment of this disclosure.

Further, as illustrated in FIG. 5, the trouser body 1a is provided with a plurality of belt loops 21 through which the waist protection belt 31 is inserted. The plurality of belt loops 21 are sewn and fixed to the circumference surface of the belt part 11. By tightening the trouser body 1a at the waist of the wearer with the waist protection belt 31 inserted through the belt loops 21, it can ensure to hold the trouser body 1a. Note the belt loops 21 are also applicable to a conventionally used belt.

Further, a left abdomen touch fastener (hook-and-loop fastener) 25 is sewn and fixed to the trouser body 1a at a position corresponding to the left abdomen portion of the belt cloth 10. Additionally, a right abdomen touch fastener (hook-and-loop fastener) 26 is sewn and fixed to the trouser body 1a at a position corresponding to the right abdomen part of the belt cloth 10.

Figure 8:
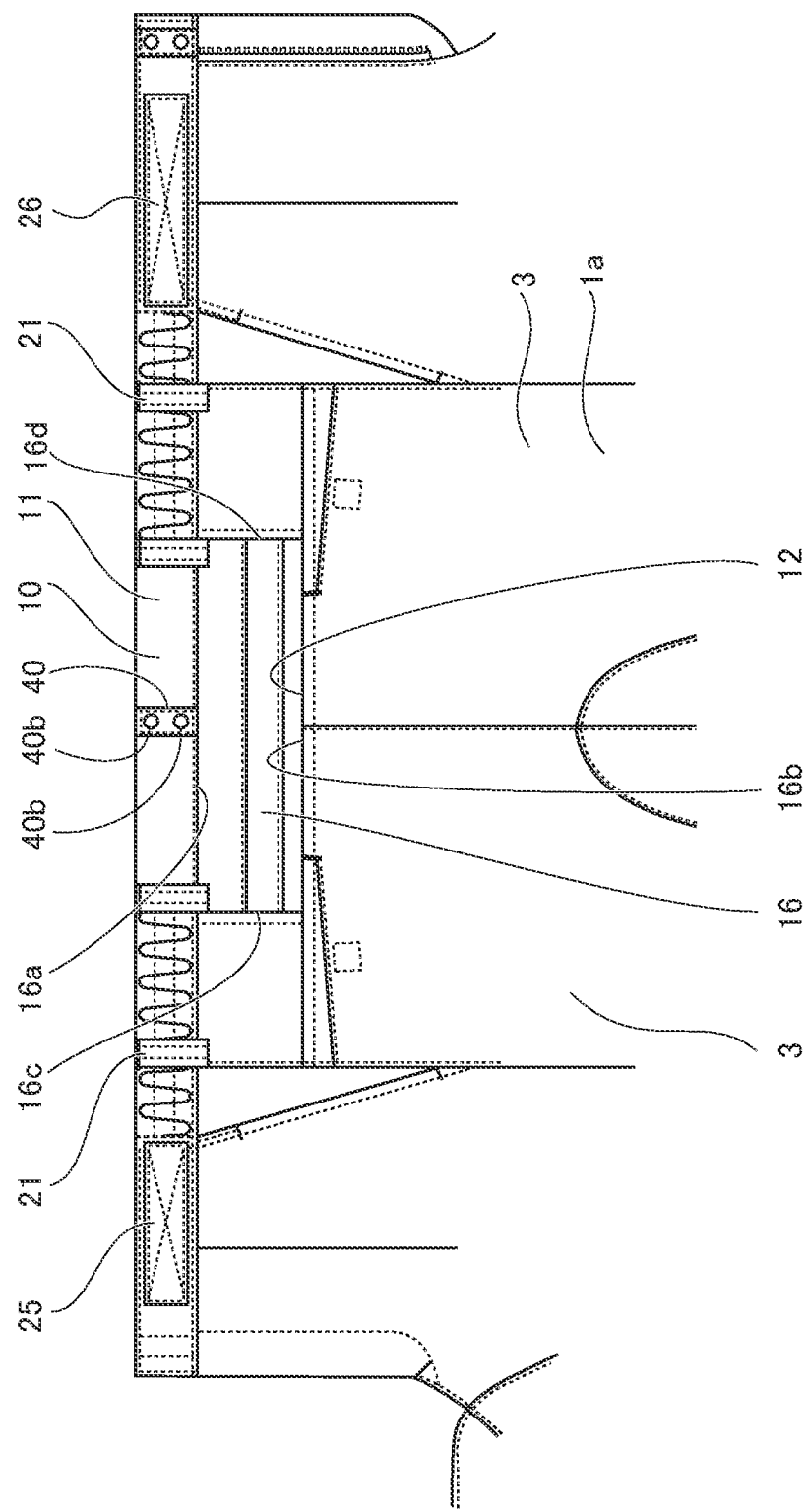
FIG. 8 is a development view illustrating the back side of the trousers according to the First Embodiment of this disclosure.
Figure 9:
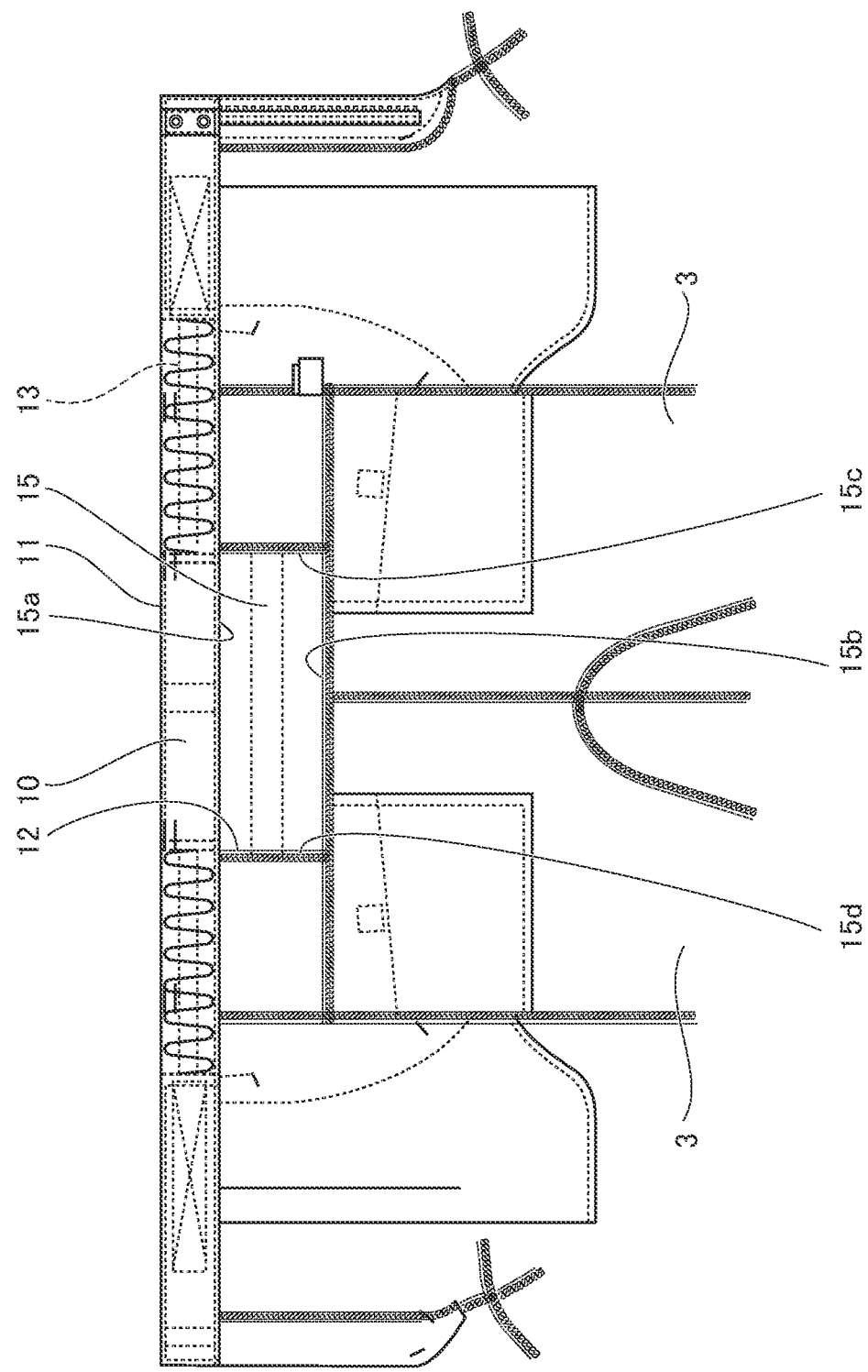
FIG. 9 is a development view illustrating the front side of the trousers according to the First Embodiment of this disclosure.

Further, as illustrated in FIGS. 8, 9, the upper portion of the back body parts 3, 3 of the trouser body 1a (to be specific, the portion from the waist part to the upper side of the buttocks part) is formed as a notch (space) 12. That is, the space 12 is formed below the belt part 11 of the back body parts 3, 3 of the trouser body 1a. The width of the space 12 is about 1.5 to 3 times the length of the sacrum width (i.e., about 30 cm) and the length of the space 12 in the vertical direction is about 1.0 to 1.5 times the length of the sacrum in the vertical direction. The space 12 is provided with the stretchable cloth 15 and the cover cloth 16. As illustrated in FIG. 9, the stretchable cloth 15 has a square shape, and an upper edge 15a of the stretchable cloth 15 is sewn to the lower part of the annular-shaped belt part 11 (i.e., the upper edge 15a of the stretchable cloth 15 is placed between the folded edges 10a, 10a of the belt cloth 10 and sewn together with the folded edges 10a, 10a) (see FIG. 6). The stretchable cloth 15 is also sewn to the back body parts 3, 3 at a lower edge 15b and both side edges 15c, 15d thereof.

The stretchable cloth 15 is made of a cloth having appropriate stretchability, elasticity, and rigidity, such as power net fabric. The power net fabric generally means fine-net knitted fabric having stretchability. The power net fabric is formed by interknitting or interlacing nylon fiber and elastic fiber of polyurethane and has excellent kickback resistance when stretched. However, the stretchable cloth 15 of this disclosure is not limited to the power net fabric.

The cover cloth 16 has a square shape having a substantially equal width dimension to that of the stretchable cloth 15 and a longer length than that of the stretchable cloth 15 in the vertical direction. As illustrated in FIG. 6, the cover cloth 16 is repeatedly folded back 180 degrees with mountain folds and valley folds at a plurality of folds 17 extending in the width direction. Thus, the cover cloth 16 is formed in a corrugated or bellows shape. In other words, the cover cloth 16 has a plurality of pleats. Here, the length of the corrugated cover cloth 16 in the vertical direction is substantially equal to the length of the stretchable cloth 15 in the vertical direction. Similar to the back body parts 3, 3, the cover cloth 16 is made of a cloth having little stretchability.

The cover cloth 16 is provided to overlap with the stretchable cloth 15 at the portion corresponding to the waist part of the wearer of the trouser body 1a. Together with the stretchable cloth 15, an upper edge 16a of the cover cloth 16 is sewn to the lower part of the annular-shaped belt part 11 (i.e., the upper edge 16a of the cover cloth 16 is placed between the folded edges 10a, 10a of the belt cloth 10 and sewn together with the folded edges 10a, 10a). The cover cloth 16 is also sewn to the back body parts 3, 3, together with the stretchable cloth 15, at a lower edge 16b and both side edges 16c, 16d thereof.

The cover cloth 16 is integrally sewn to the stretchable cloth 15 at seams 18 which extend over the entire length of the cover cloth 16 in the longitudinal direction. The seams 18 are provided at or in the vicinity of the valley folds 17B, 17D which are in the even numbers from the top among the folds 17 (i.e., valley fold 17B is second fold, and valley fold 17D is fourth fold). Further, the cover cloth 16 is provided with seams 19 which extend over the entire width of the cover cloth 16. The seams 19 are provided in the vicinity of the first fold 17A and the third fold 17B of the cover cloth 16. Accordingly, the parts of the cover cloth 16 are overlapped with each other. With this configuration, the shapes of the folds 17A, 17C are maintained. As the cover cloth 16 forms pleats, the cover cloth 16 has low color fading. Further, as the seams 18 are covered by the part of the cover cloth 16, it can prevent the seams 18 from being cut.

When the upper edges 15a, 16a of the stretchable cloth 15 and the cover cloth 16 and the lower edges 15b, 16b of the stretchable cloth 15 and the cover cloth 16 are each pulled in the opposite directions of the vertical direction, the stretchable cloth 15 elastically deforms and the cover cloth 16 extends in the vertical direction as the corrugated parts of the cover cloth 16 expand. As described above, the stretchable cloth 15 is integrally provided with the cover cloth 16. Therefore, when the corrugated parts of the cover cloth 16 fully expand and the folds 17 disappear from the cover cloth 16 (i.e., when the cover cloth 16 cannot expand in the vertical direction any further), the stretchable cloth 15 also cannot extend in the vertical direction any further.

A waist stretchable part 20 is formed of the stretchable cloth 15 and the cover cloth 16. The stretchable cloth 15 is provided inside of the cover cloth 16 (i.e., on waist side of wearer of trouser body 1a) and is overlapped by the cover cloth 16. That is, the stretchable cloth 15 is hid by the cover cloth 16 when viewed from the outside of the trouser body 1a. In other words, the stretchable cloth 15 of the trousers 1 is not visible from the outside. Hence, the appearance of the trousers is not affected by the stretchable cloth 15. Further, as the cover cloth 16 is formed to have the corrugated shape, it is possible to expand the cover cloth 16 from the state where the corrugated parts are folded, and thereby it does not interrupt the extension and construction of the stretchable cloth 15.

The trousers with the waist protection belt (1) can prevent backache, reduce backache, and/or protect the waist after an occurrence of backache by the waist protection belt 31 attached to the belt cloth 10. Further, as the waist protection belt 31 is integrally provided with the trouser body 1a, it can prevent the trouser body 1a from being bulky. Additionally, it is hard to be torn apart or to be ripped while it ensures comfortability and does not disrupt movement of the wearer of the trouser body 1a.

Figure 18:
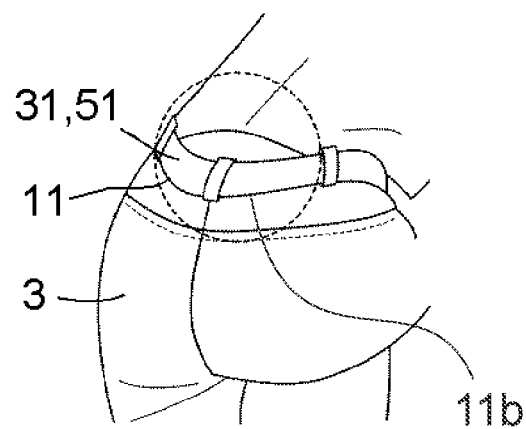
FIG. 18 is an explanatory view illustrating a posture in which a wearer of the conventional trousers with the waist protection belt is bending his or her waist forward.

In general, trousers are designed and manufactured based on a standing posture of a wearer, and thus the vertical dimensions of the front and back body parts are set substantially equal to each other. Therefore, with conventional trousers, when the wearer changes his posture from the standing posture to the seated posture or to the crouching posture and the skin of the waist and back of the wearer stretches, the cloth of the trousers cannot follow the stretch of the skin. As a result, the back part of the trousers (i.e., back body part 3 and belt part 11) slides down (see FIGS. 18 and 19). That is, if the conventional belt or the waist protection belt 31 is attached to the belt cloth of the conventional trousers, the belt or the waist protection belt 31 also slides down in accordance with the postures of the wearer.

Figure 10:
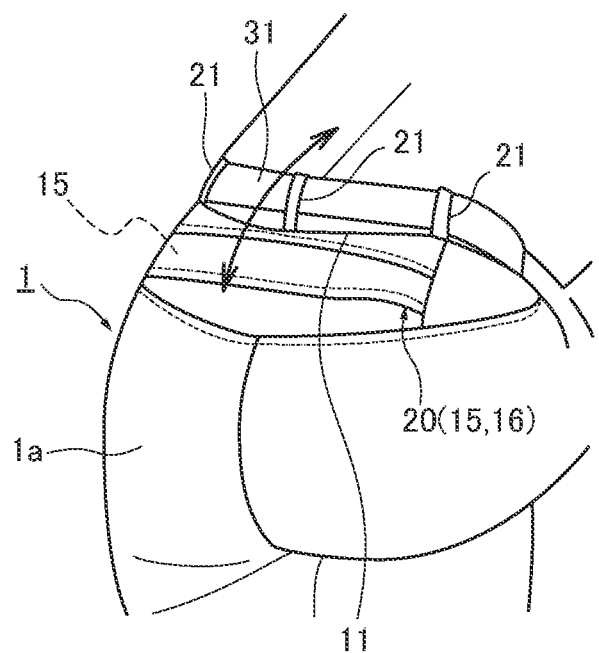
FIG. 10 is an explanatory view illustrating a posture in which a wearer of the trousers with the waist protection belt according to the First Embodiment of this disclosure is bending his or her waist forward.
Figure 11:
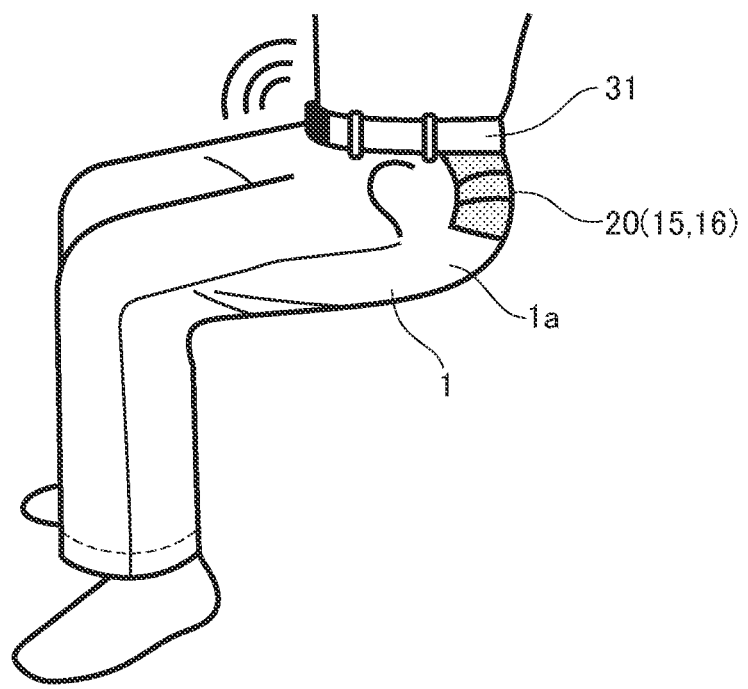
FIG. 11 is an explanatory view illustrating a posture in which the wearer of the trousers with the waist protection belt according to the First Embodiment of this disclosure is seated.

In contrary, the trousers with the waist protection belt (1) according to the First Embodiment of this disclosure are provided with the stretchable cloth 15 on the trouser body 1a. Accordingly, as illustrated in FIGS. 10 and 11, the stretchable cloth 15 and the cover cloth 16 appropriately extend or stretch when the trouser body 1a is pulled downward as the wearer of the trousers with the waist protection belt (1) crouches. That is, the belt part 11 of the trousers is not pulled downward. In other words, since the wearing position of the waist protection belt 31 does not change or move, it is possible to hold and maintain the wearing position of the waist protection belt 31 at the pelvic position of the wearer. As a result, it can ensure the performance of the waist protection belt 31. Further, since the stretchable cloth 15 extends and follows the stretch of the skin on the waist part when the wearer changes his/her posture, it is possible to ensure the motion performance of the wearer and also does not impair the comfortability of the trousers.

Further, the stretchable cloth 15 is provided at the trouser body 1a by sewing the upper edge 15a of the stretchable cloth 15 to the belt cloth 10 and by sewing the lower edge 15b of the stretchable cloth 15 to the back body part 3. That is, the stretchable cloth 15 is provided between the waist protection belt 31 and the trouser body 1a. With this, it is possible to ensure the comfortability of the trousers.

In the trousers with the waist protection belt (1), the stretchable cloth 15 and the cover cloth 16 are provided at a position corresponding to the waist part of the wearer. Therefore, the stretchable cloth 15 and the cover cloth 16 are inconspicuous. Further, the stretchable cloth 15 and the cover cloth 16 extend and construct in accordance with the motion taken by the wearer. Accordingly, the wearer can easily perform exercise, and it also ensures to prevent the waist protection belt 31 from moving and sliding. Further, since the stretchable cloth 15 is excellent in pilling resistance and in snagging resistance, the trousers 1 are wearable for a long period of time.

It should be noted that in this disclosure, the term "waist part" represents the vicinity of a protruding part of the pelvic (i.e., so-called "anterior superior iliac spine") of the wearer of the trousers 1. The waist protection belt 31 exhibits the best effect on prevention of backache when the waist protection belt 31 is worn at the waist part.

In order to effectively exhibit the effect, the inseam of the trousers 1 (i.e., portion from lower end of belt cloth 10 to upper end of crotch part) in the First Embodiment is designed to be significantly shallow. To be specific, the inseam is about 5 cm shorter than that of the conventional trousers. With this, the belt cloth 10 is naturally positioned at the waist part when the trousers 1 are worn. By positioning the belt cloth 10 at the waist part, the waist protection belt 31 is also positioned at the waist part, thereby the effect on waist protection is improved.

The belt cloth of the conventional trousers is positioned between the waist and the pelvic. That is, if a waist protection belt is attached or installed to the conventional belt cloth, it is hardly possible to obtain the effect on reducing backache and the effect on waist protection. However, in the First Embodiment, the inseam of the trousers 1 is designed to be shallow so as to position the belt cloth at the pelvic position. Accordingly, when the waist protection belt 31 is worn like a normal waist belt, the waist protection belt 31 can cover the pelvic position. As a result, it becomes possible to exhibit the effect on reducing backache and the effect on waist protection.

With conventional trousers, if the inseam is designed to be shallow, the waist part of the trousers would be pulled downward when the wearer takes a seated posture or a crouching posture. However, the trousers with the waist protection belt (1) includes the waist stretchable part 20 (i.e., stretchable cloth 15 and cover cloth 16) at the waist part. Therefore, the position of the belt cloth 10 of the trouser body 1a does not move downward from the waist part. That is, when the wearer takes the seated posture or the crouching posture, the waist stretchable part 20 appropriately extends, as illustrated in FIG. 10. Therefore, the position of the waist protection belt 31 does not slide down from the waist part and is maintained at the position corresponding to the waist part such that the waist protection belt 31 is kept at the waist part to surround the circumference thereof. As described above, the waist protection belt 31 can appropriately tighten only the position corresponding to the waist part, and thereby steadily exhibiting the effect on the waist protection.

Figure 19:
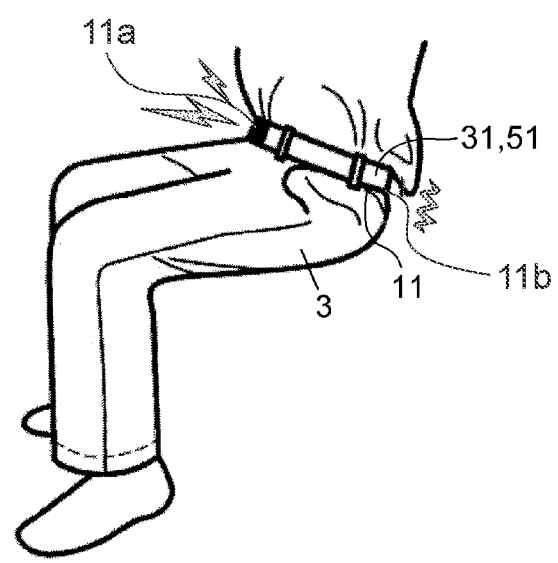
FIG. 19 is an explanatory view illustrating a posture in which the wearer of the conventional trousers with the waist protection belt is seated.

Additionally, as illustrated in FIG. 19, with the conventional trousers which do not have the waist stretchable part 20 (i.e., stretchable cloth 15 and cover cloth 16), the trousers cannot follow the stretch of skin on the waist part and/or the buttocks part when the wearer takes the seated posture or the crouching posture. Therefore, the rear belt part 11b of the trousers slides downward and may create a gap between the rear belt part 11b and the waist part of the wearer. Resultantly, the wearer's shirt may come out from the gap. Further, when the rear belt part 11b is pulled downward, the front belt part 11a may excessively press the abdomen part of the wearer.

However, with the trousers 1 of the embodiment, the stretchable cloth 15 extends appropriately to follow the stretch of the skin when the wearer takes the seated posture or the crouching posture. As a result, it can prevent the rear belt part 11b from sliding downward to create a gap between the rear belt part 11b and the waist part of the wearer, and also it can reduce the pressure applied to the abdomen part of the wearer generated by the belt part 11 (to be specific, front belt part 11a) of the trousers with the waist protection belt (1). Here, even without the waist protection belt 31 but with a normal belt, the trousers can suppress the application of excessive abdominal pressure to the abdomen part so as to prevent the backache and/or to reduce the backache since it can ensure to maintain the position of the belt part 11 at the pelvic position of the wearer.

When the wearer of the trousers 1 takes the crouching posture, the extension amount of the skin increases from the waist part to the buttocks part (i.e., from top to down). In other words, the extension rate is larger at the lower portion of the buttocks part than the upper portion of the buttocks part. Therefore, as illustrated in FIG. 6, the stretchable cloth 15 of this embodiment is configured to extend further at the upper portion of the waist stretchable part 20 (i.e., the portion between the upper edge 15a of the stretchable cloth 15 and a connection part of the stretchable cloth and cover cloth 18A) than at the lower portion of the waist stretchable part 20 (i.e., the portion between the connection part of the stretchable cloth and cover cloth 18A and a connection part of the stretchable cloth and cover cloth 18B). With this, it is possible to reduce the sense of discomfort at the abdomen part and/or the buttocks part and to reduce the pressure applied to the abdomen part. As a result, it becomes possible to prevent the backache.

Further, when the skin on the waist part of the wearer extends or stretches as the wearer of the trousers 1 bends his/her waist forward, the cover cloth 16 expands and stretches in accordance with the stretch of the stretchable cloth 15. With this, it can ensure that the stretchable cloth 15 does not get exposed, as well as it can reduce or even prevent the gap between the rear belt part 11b of the belt part 11 of the trousers 1 and the waist part of the wearer.

Accordingly, it can prevent the exposure of the waist part, and thus can keep the temperature of the abdomen part. Further, it can prevent dirt, debris, sparks, etc. from getting inside the trousers 1 through such a gap during the operation. Additionally, it can prevent the wearer's shirt from coming out from the trousers 1, and therefore it can avoid the shirt to get caught by, for example, a machine. With the stretchable cloth 15, the wearer can easily take the crouching posture even when the wearer sweats and the trousers 1 stick to the skin of the wearer.

With the trousers with the waist protection belt (1) of this embodiment, workers who have backache, who may get backache, or even who does not currently have backache can safely, without impairing the function of the waist protection belt 31, perform works which may become a cause of backache, such as handling heavy materials, works with an incorrect posture (e.g., a half-crouching posture, forward bending posture), works with a seated posture for a long period of time, and works while receiving whole body vibration. Therefore, the trousers with the waist protection belt (1) according to the embodiment is applicable and suitable as light-work trousers for the workers who perform light works such as desk works, works at a supermarket, works at an electronics retails store, works performed by a waiter, works performed by a chef or a cook, works performed by staff working at a pachinko parlor, and works of a professional cleaning service.

Figure 12A:
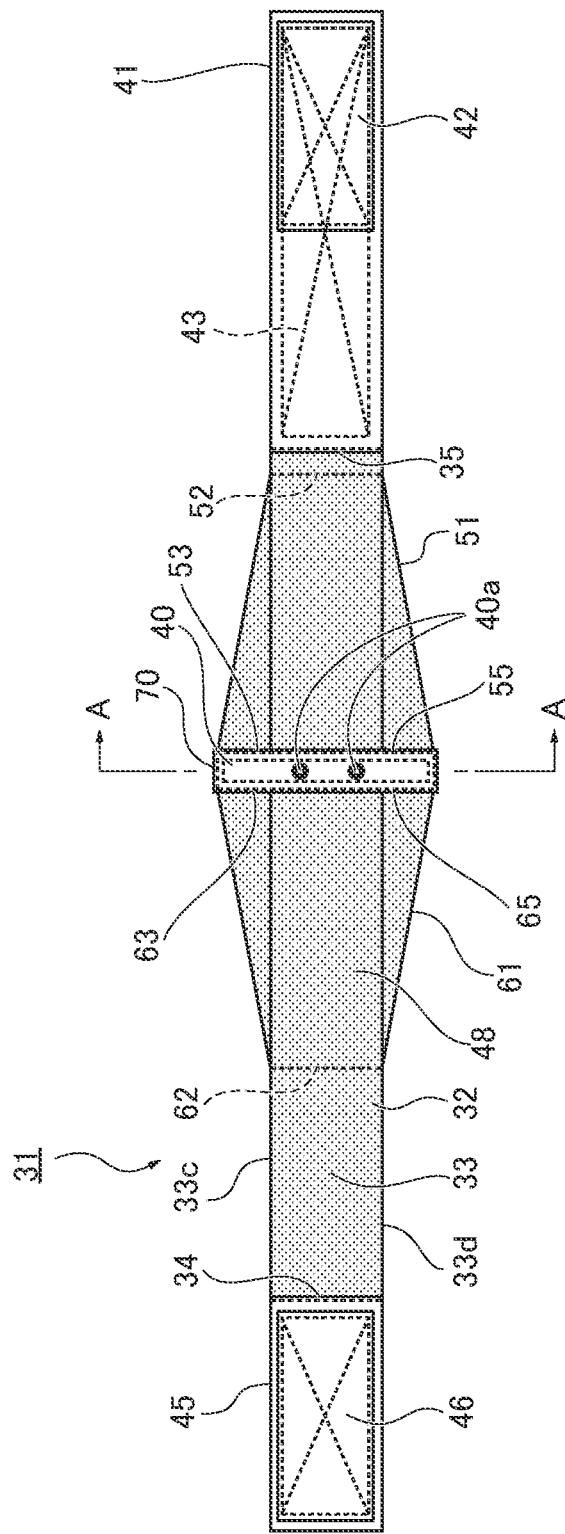
FIG. 12A is a front view illustrating the waist protection belt according to the First Embodiment of this disclosure.
Figure 12B:
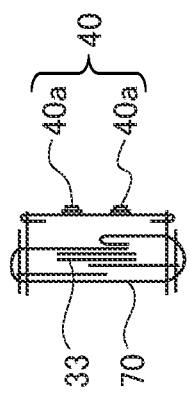
FIG. 12B is a right side view illustrating the waist protection belt according to the First Embodiment of this disclosure.

As illustrated in FIGS. 8, 12A, 12B, the waist protection belt 31 includes a detachable part 40 provided on the back surface of the waist part of the belt cloth 10. With the detachable part 40 on the back surface of the waist part of the belt cloth 10, the waist protection belt 31 can be removed from the trouser body 1*a*. That is, it is possible to wash the trousers 1 and the waist protection belt 31 separately and also possible to replace the waist protection belt 31 when needed. The detachable part 40 may be configured by snap buttons, for example. To be specific, the detachable part 40 may include male fasteners 40*a*, 40*a* and female fasteners 40*b*, 40*b*, which are detachably fixed to the male fasteners 40*a*, 40*a*. In this case, one of a group of the male fasteners 40*a*, 40*a* and a group of the female fasteners 40*b*, 40*b* (in the example illustrated in FIGS. 13A-13D, the male fasteners 40*a*) is provided at the waist protection belt 31, and the other one of the group of the male fasteners 40*a*, 40*a* and the group of the female fasteners 40*b*, 40*b* (in the example illustrated in FIGS. 12A, 12B, the female fasteners 40*a*) is provided at the back surface of the waist part of the belt cloth 10. By fixing one of the group of the male fasteners and the group of the female fasteners provided at the waist protection belt 31 (i.e., the male fasteners) to the other one of the group of the male fasteners and the group of the female fasteners provided on the back surface of the waist part of the belt cloth 10 (i.e., the female fasteners), the waist protection belt 31 is detachably attached to the belt cloth 10. Here, the waist protection belt 31 may be sewn to and attached to the belt cloth 10.

As described above, the waist protection belt 31 according to the embodiment is configured to be attached to the outer surface of the trouser body 1*a*. When a waist protection belt is worn and installed inside trousers, the wearer needs to take off the trousers to replace or readjust the waist protection belt. However, since the waist protection belt 31 according to the embodiment is configured to be attached to the outer surface of the trouser body 1*a*, the wearer can tighten or loosen the waist protection belt 31 without removing the trousers 1 if needed. Further, as described later, the wearer can freely adjust the tightness of the waist protection belt 31. Additionally, since the waist protection belt 31 is not positioned inside the trousers 1, it can reduce the sense of discomfort while the waist protection belt 31 is worn.

As illustrated in FIGS. 12A, 12B, 13A-13D, the waist protection belt has a belt main body 32. The belt main body 32 includes a stretchable main belt 33, and a stretchable left-side auxiliary belt 51 and a stretchable right-side auxiliary belt 61 which are sewn to the left side and the right side of the main belt 33, respectively. The left-side auxiliary belt 51 and the right-side auxiliary belt 61 are each formed in a substantially V-shape.

The main belt 33 is formed by superposing two rubber bands each having a width of about 5.5 cm and a length of about 60 cm. The right end 34 of the main belt 33 is sewn with a right connection band 45. The right connection band 45 is formed by folding a non-stretchable cloth to have a width of about 5.5 cm and a length of about 27 cm, and then sewn together with the right end 34 of the main belt 33. The entire inner surface (i.e., surface facing wearer) of the right connection band 45 is provided with a right-side touch fastener 46.

The left end 35 of the main belt 33 is sewn with a left connection band 41. The left connection band 41 is formed by folding a non-stretchable cloth to have a width of 5.5 cm and a length of 15 cm, and then sewn together with the left end 35 of the main belt 33. The inner surface (i.e., surface facing wearer) of the left connection band 41 is partially (in the example illustrated in the drawings, about a half of the surface on the left) provided with a first left-side touch fastener 42. Further, the entire outer surface (i.e., surface facing outside) of the left connection band 41 is provided with a second left-side touch fattener 43.

It should be noted that it is said to be necessary at least to support the pelvic part and to properly maintain the abdominal pressure at the front abdomen part in order to sufficiently protect the waist part by using the waist protection belt 31. Since it is desirable for the waist protection belt 31 not to limit the movement of the wearer as much as possible and it is designed to be attached to the belt part 11 of the trouser body 1*a*, the width of the waist protection belt 31 according to the embodiment is set within a range of 4.8 to 11 cm. As described later, the auxiliary belts 51, 61 are overlapped with the main belt 33 to widely cover the pelvic at the waist-back part since the waist-back part should require a wider width. Here, the waist protection belt 31 according to the embodiment does not include a support member. The waist protection belt 31 realizes to properly maintain the abdominal pressure by overlapping the end parts of the main belt 33 each other and by firmly fixing them using the fasteners (first left-side touch fastener 42, second left-side touch fastener 43, and right-side touch fastener 46).

As illustrated in FIGS. 12A, 12B, 13A-13D, the waist protection belt 31 forms a main band part 48 by the left connection band 41, the main belt 33, and the right connection band 45, and the length from the left end of the left connection band 41 to the right end of the right connection band 45 is about 1 m. The center part of the main band part 48 is shifted to the side of the right connection band 45 with respect to the center of the main belt 33.

The left-side auxiliary belt 51 is folded to have the substantially V-shape, and the fold 52 is sewn to the left side of the main belt 33. As the left-side auxiliary belt 51 has substantially the same width as the main belt 33, the fold 52 does not protrude from an upper edge 33*c* and a lower edge 33*d* of the main belt 33. The both ends 53, 55 of the left-side auxiliary belt 51 are extended substantially to the center of the main band part 48 and are sewn to a connection cloth 70 together with the main belt 33. As the both ends 53, 55 are folded in the substantially V-shape, the both ends 53, 55 protrude from the upper edge 33*c* and the lower edge 33*d* of the main belt 33. Here, the connection cloth 70 is made of a non-stretchable cloth having about 2.5 cm in width.

The right-side auxiliary belt 61 is folded to have the substantially V-shape, and the fold 62 is sewn to the right side (to be specific, right end 35) of the main belt 33. As the right-side auxiliary belt 61 has substantially the same width as the main belt 33, the fold 62 does not protrude from either the upper edge 33*c* or the lower edge 33*d* of the main belt 33. The both ends 63, 65 of the right-side auxiliary belt 61 are extended substantially to the center of the main band part 48 and are sewn to the connection cloth 70 together with the main belt 33. As the both ends 63, 65 are folded in the substantially V-shape, the both ends 53, 55 protrude from the upper edge 33*c* and the lower edge 33*d* of the main belt 33.

In general, a waist protection belt is configured such that the center portion of the waist part of the belt is formed to be the widest part to cover the entire pelvic. Further, as the waist-back part of a human being has a large muscle quantity and has a strong bony support, it is not necessary to press the waist-back part. Instead, a waist protection belt generally includes a hard member such as an elastic core material and a supporting member to support the muscles of the back and to stabilize the spinal column. Similarly, the waist protection belt 31 of this embodiment is configured to include the V-shaped auxiliary belts 51, 61 to have the center portion of the waist part of the belt be the widest part. Further, by including the connection bands 41, 51 at the inside and the outside of the position corresponding to the abdomen part, the waist protection belt 31 of this embodiment achieves the thick and hard structure to support the muscles of the back and to stabilize the spinal column.

The waist protection belt 31 is attached to the belt cloth 10 such that the substantially center part in the longitudinal direction of the belt 31 is attached to the position corresponding to the waist part of the belt cloth 10. The waist protection belt 31 is defined to have the length such that the both ends thereof are overlapped with each other and the second left-side touch fastener 43 and the right-side touch fastener 46 are designed to be at the overlapped position when the waist protection belt 31 is used. That is, the second left-side touch fastener 43, which is provided at the left end side of the waist protection belt 31, is detachably connected to the right-side touch fastener 46, which is provided at the right end side of the waist protection belt 31, so as to protect the waist part. Note that the second left-side touch fastener 43 is provided on the other side of the first left-side touch fastener 42 (i.e., on the outer side).

Figure 14:
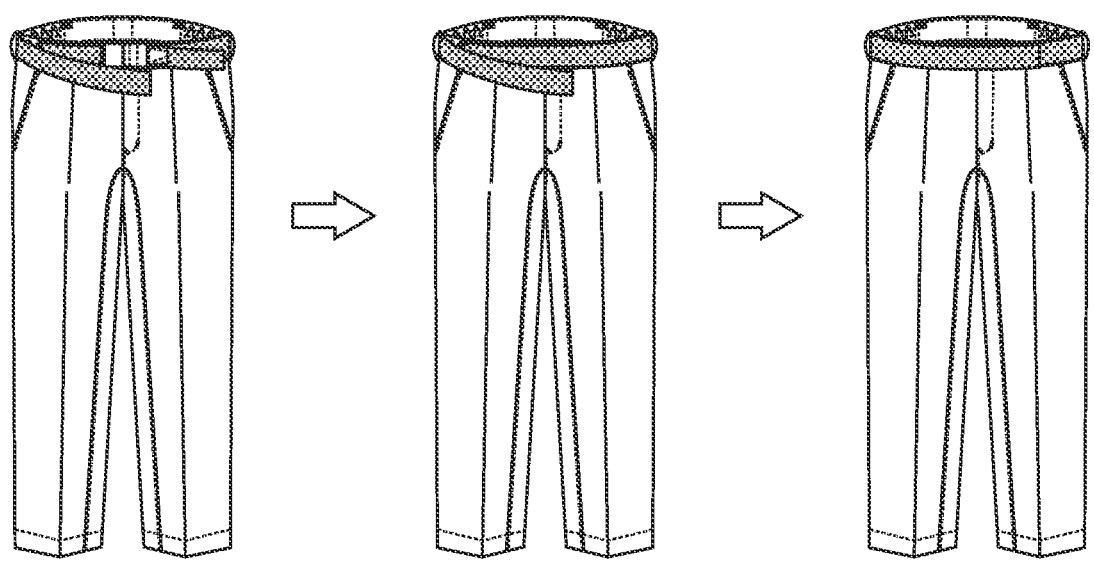
FIG. 14 is an explanatory view showing how to wear the waist protection belt according to the First Embodiment of this disclosure.

Next, a method to wear the waist protection belt 31 will be explained with reference to FIG. 14 and so on.

Figure 2:
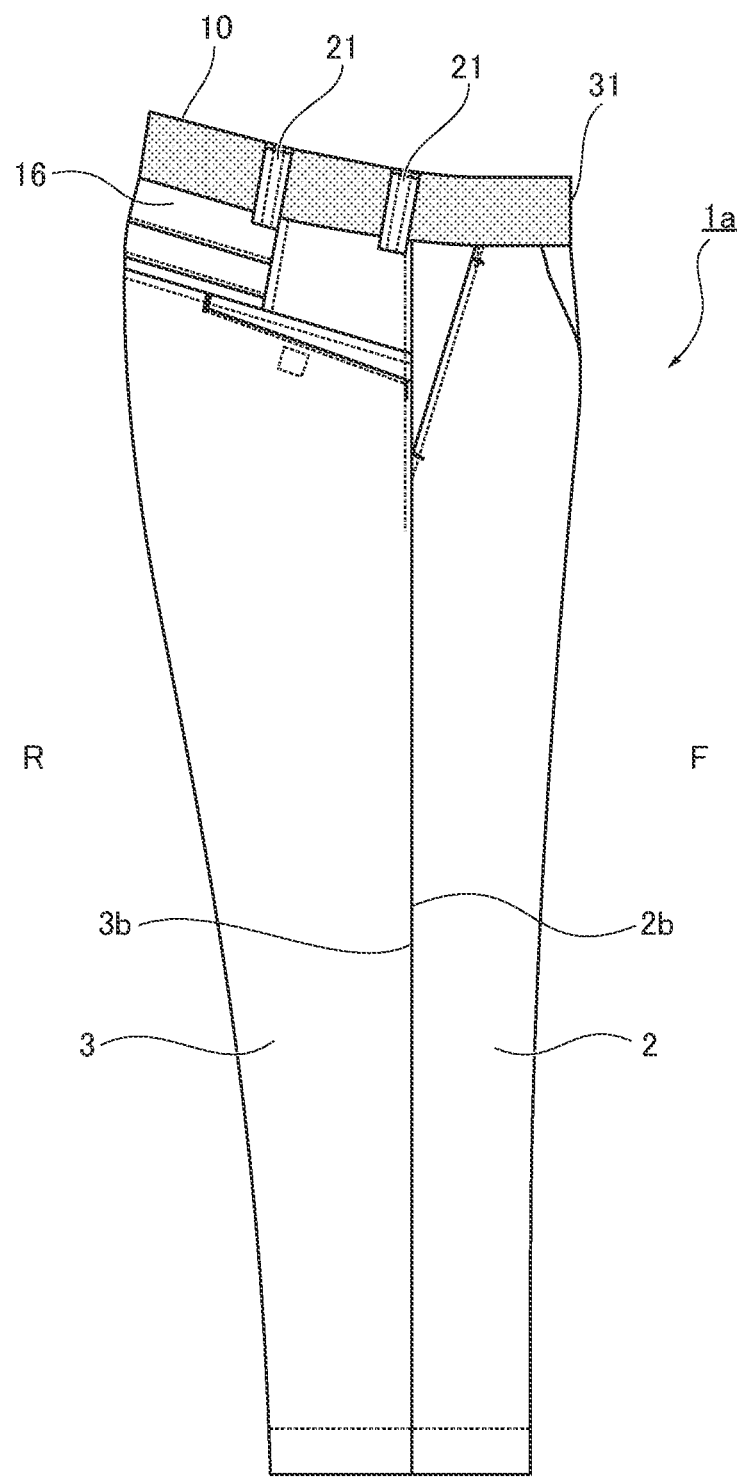
FIG. 2 is a left side view illustrating the trousers with the waist protection belt according to the First Embodiment of this disclosure.
Figure 3:
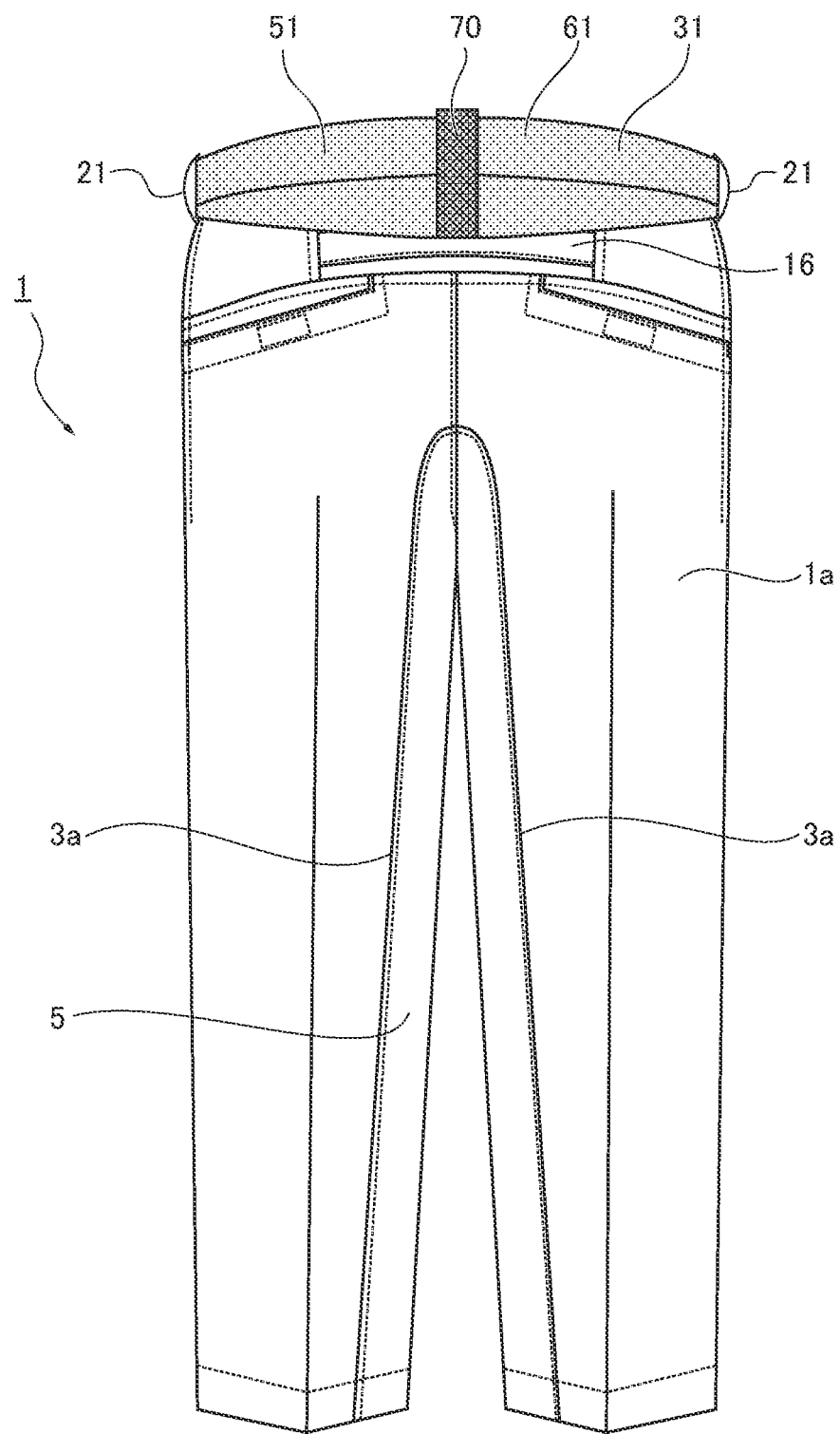
FIG. 3 is a back view illustrating the trousers with the waist protection belt according to the First Embodiment of this disclosure.

The trousers with the waist protection belt (1) are worn in the same manner as normal trousers. As illustrated in FIGS. 1 to 3, the left connection band 41 and the right connection band 45 are inserted through the belt loops 21. Next, as illustrated in FIG. 14, the main belt 33 and the left-side auxiliary belt 51 are pulled and stretched against their own elastic forces so as to pull out the left connection band 41, and the first left-side touch fastener 42 of the left connection band 41 is detachably connected and fixed to the left abdomen touch fastener 25 and/or to the right abdomen touch fastener 26. Accordingly, it is possible to position (provisionally tighten) the waist protection belt 31 with respect to the trouser body 1*a* (belt part 11).

Subsequently, the main belt 33 and the right-side auxiliary belt 61 are pulled and stretched against their own elastic forces so as to pull out the right connection band 45, and the right-side touch fastener 46 of the right connection band 45 is detachably connected and fixed to the second left-side touch fastener 43 of the left connection band 41. Accordingly, the waist protection belt 31 of the trousers 1 is worn and can appropriately apply pressure around the entire abdomen part. As the second left-side touch fastener 43 is long in the width direction, it is possible to adjust the elastic forces generated by the main belt 33, the left-side auxiliary belt 51, and the right-side auxiliary belt 61 by changing the attaching position of the right connection band.

Conventional waist protection belts are generally configured such that the end parts thereof are overlapped on the abdominal side and fixed to each other by, for example, touch fasteners to tighten around the entire abdomen part. That is, without overlapping the waist protection belt at least partially, it is difficult to keep the abdominal pressure at constant, and therefore, it is difficult to sufficiently reduce backache and/or to prevent such backache. Similarly, the waist protection belt according to the embodiment is configured such that the end parts thereof are overlapped and fixed to each other to appropriately tighten around the entire abdomen part.

Further, recently used waist protection belts include an auxiliary belt provided at each of the outer sides of the belt main body. That is, after tightening the belt main body, the waist protection belt is further tightened by the auxiliary belts to further stabilize the pelvic of the wearer. In this embodiment, the waist protection belt 31 is configured to be provisionally tightened (i.e., positioned) using the abdomen touch fasteners 25, 26 of the belt part 11 of the trousers 1 and the first left-side touch fastener 42 of the waist protection belt 31, and then to be fully tightened by overlapping and fixing the end parts of the waist protection belt 31 (i.e., second left-side touch fastener 43 and right-side touch fastener 46). Accordingly, it is possible to firmly tighten the pelvic by the belt part 11 of the trousers 1 and the waist protection belt 31. In other words, the trousers 1 and the waist protection belt 31 achieve the similar advantageous effects to the conventional waist protection belt and the auxiliary belts.

The waist protection belt 31 according to this embodiment protects the waist part by directly attaching the connection cloth 70 to the waist part. To be specific, the both ends 53, 55, 63, 65 of the auxiliary belts 51, 61 are respectively sewn to the upper and lower positions of the connection cloth 70 centering the main belt 33 so as to have a wider shape with the main belt 33 and the auxiliary belts 51, 61. Accordingly, the waist part is not partially supported by only the main belt 33, but is entirely supported by the main belt 33 and the auxiliary belts 51, 61. Therefore, it is possible to reduce the backache and/or to efficiently protect the waist part, resulting in giving further sense of piece and safety.

Further, the trousers with the waist protection belt (1) include the waist protection belt 31 and the trouser body 1*a* to which the waist protection belt 31 is detachably attached. Therefore, it is possible to adjust the design of the trouser body 1*a* in accordance with the shape of the waist protection belt 31. Resultantly, it is possible to fabricate the appearance of the trouser body 1*a* and to have an impressive appearance.

It should be noted that the main belt 33 is illustrated to be positioned inside (i.e., on wearer side) and the left-side and right-side auxiliary belts 51, 61 are illustrated to be positioned outside (i.e., on other side of wearer) in FIGS. 11, 12A, 12B. However, the structure of the waist protection belt 31 according to this disclosure is not limited thereto. For example, the main belt 33 may be positioned outside, and the left-side and right-side auxiliary belts 51, 61 may be positioned inside. In such a case, the main belt 33 may include decorations such as a piece of embroidery and a logo on the outer surface thereof to make the appearance of the waist protection belt 31 impressive. Additionally, the waist protection belt 31 may be configured to be reversible such that the wear can select the appearance in accordance with his/her preference.

As illustrated in FIGS. 9, 15, the trouser body 1*a* includes a pair of back pockets 22, 23 at the positions corresponding to the left and right buttocks parts. The back pockets 22, 23 are piped pockets and are provided, for example, at positions located below the left and right ends of the stretchable cloth 15 and the cover cloth 16, respectively. As illustrated in another variation of FIG. 15, the stretchable cloth 15 and the cover cloth 16 may be preferably provided such that the positions of the left ends 15*c*, 16*c* correspond to the center line of the left-side back pocket 22, and the positions of the right ends 15*d*, 16*c* correspond to the center line of the right-side back pocket 23.

In general, trousers for light works have the upper end thereof (i.e., waist part) at a position lower than the waist part of the human being, and the openings of the back pockets 22, 23 are positioned lower than the middle-hips (i.e., height between waist part and hip part). The peripheral length of the hips is about 25% longer than the peripheral length of the waist part. That is, by making the positions of the both ends of the stretchable cloth 15 and the cover cloth 16 correspond to the centers of the back pockets 22, 23, the width of the stretchable cloth 15 and the cover cloth 16 becomes relatively narrow.

FIG. 20 shows a first reference material. The first reference material is a graph showing the results of experiments performed to confirm the preferable effects on the configuration in which the both ends of the stretchable cloth 15 and the cover cloth 16 correspond to the centers of the back pockets 22, 23. Note that the subject of the experiments has a height of 169 cm and a waist of 80 cm, and was wearing L size (i.e., 80 to 85 cm round the waist) trousers. The distance between the centers of the back pockets of the trousers is set to 27.3 cm. In FIG. 20, the solid line shows the result in which the subject took the crouching posture, and the dashed line shows the result in which the subject took the seated posture.

In this experiment, the extension amounts of the skin on the back body part when the subject changed his/her position from the standing posture to the crouching posture or to the seated posture were measured. In FIG. 20, the center corresponds to the position of the spine (i.e., center of back body part), and the numbers on the horizontal axis shows the distances from the spine position to the measuring point in the left and right direction. The vertical axis shows the extension amounts of the skin. As the distance between the centers of the back pockets 22, 23 is set to 27.3 cm, the distance from the center position of each back pocket 22, 23 to the center of the back body part is about 13.7 cm.

As shown in the graph, when the subject took the crouching posture, the extension amount of the skin at the center of the back body part was 1.7 cm. However, the extension amount of the skin at the position 8.1 cm away from the center was reduced to about the half, and the extension amount of the skin at the position about 13.5 cm away from the center was zero (0). Similarly, when the subject took the seated posture, the extension amount of the skin at the center of the back body part was 1.2 cm. However, the extension amount of the skin at the position 8.1 cm away from the center was reduced to about the half, and the extension amount of the skin at the position about 13.5 cm away from the center was zero (0). From the results of this experiment, it should be understood that the stretchable cloth 15 is not required at the position 13.5 cm away from the center of the back body part.

As described above, by making the width of the stretchable cloth 15 substantially equal to the distance between the centers of the back pockets 22, 23 (i.e., 27.3 cm), the edges of the stretchable cloth 15 are located at the positions about 13.7 cm away from the center of the back body part. As a result, the stretchable cloth 15 is appropriately provided in the area in which the skin extends, while the stretchable cloth 15 is not provided in the area in which the skin does not extend. Therefore, it can eliminate the tension of the cloth of the trousers caused by the extension of the skin in the crouching posture using the minimum and optimized stretchable cloth 15, and thereby the trousers 1 can minimize the usage of the stretchable cloth 15.

In general, the arrangements of the back pockets 22, 23 are similar to each other regardless of the types of the trousers. With the above-mentioned experiment, the inventors of this disclosure discover that the point at which the extension amount of the skin becomes zero (0) is positioned around the center of each back pocket 22, 23 regardless of the types of the trousers. That is, by making the length of the stretchable cloth 15 of the trousers 1 equal to the distance between the centers of the back pockets 22, 23, it is possible to reduce the tension at the rear belt part 11*b* in the seated posture, to prevent the rear belt part 11*b* from sliding down in the seated posture, and to reduce the abdominal pressure by the front belt part 11*a* with the minimum length (width) of the stretchable cloth 15.

FIG. 21 (second reference material) shows measurement results for the clothing pressures at the abdominal part and the waist part of the wearer of the trouser body 1*a*. The measurements of the clothing pressures were carried out by installing pressure sensors between the belt part 11 and the belt when the wearer worn the trouser body 1*a* or conventional trousers with the belt passed through the belt loops 21 on the belt part 11 and appropriately tightened the belt to prevent the trouser body 1*a* or the conventional trousers from sliding down.

As illustrated in FIGS. 22A, 22B (third reference material), the installation points for the pressure sensors are a point directly below the left scapula (P1), a point directly below the left axillary (P2), a point directly below the left nipple (P3), a point on the medial line (P4), a point directly below the right nipple (P5), a point directly below the right axillary (P6), and a point directly below the right scapula (P7). That is, there are seven (7) installation points. The pressures between the belt and the belt part are measured by the pressure sensors when the wearer was taking the standing posture, the kneeling posture, and the seated posture. Note that the pressure measurement was omitted when the wearer was taking the standing posture while only wearing the trouser body 1*a*.

There were two (2) wearers (subjects), A and B. The subject A is a male with a height of 172 cm, weight of 78 kg, and a waist of 88 cm. The subject B is a male with a height of 169 cm, weight of 72.5 kg, and a waist of 90 cm. Note that the values (with unit of kPa) in FIG. 21 represent the average of the measured values taken during 10 seconds of the measuring time. To be specific, the pressures were measured at every second for 10 seconds, and thus the average value shows the average of the measured 11 values.

In FIG. 21, the table (I) shows the measurement results (measurement results at seven measuring points) measured when the subject A worn conventional trousers and took the standing posture, the kneeling posture, and the seated posture. The table (II) shows the measurement results (measurement results at seven measuring points) measured when the subject A worn the trouser body 1*a* and took the kneeling posture and the seated posture. The table (III) shows the measurement results (measurement results at seven measuring points) measured when the subject B worn conventional trousers and took the standing posture, the kneeling posture, and the seated posture. The table (IV) shows the measurement results (measurement results at seven measuring points) measured when the subject B worn the trouser body 1*a* and took the kneeling posture and the seated posture.

As clearly shown in FIG. 21, the measured pressures (clothing pressures) measured by the pressure sensors when the wearer was in the kneeling posture or in the seated posture are greater than the pressures when the wearer was in the standing posture. Further, although there are individual differences between the subjects A, B, the clothing pressures at the front side of the wearer (i.e., pressure on abdomen part) with the trouser body 1a are smaller than the clothing pressures at the abdomen part with the conventional trousers, especially when the wearer was in the kneeling posture. Although not as dramatically reduced as in the kneeling posture, when the wearer was in the seated posture, the clothing pressures at the front side of the wearer (i.e., pressure on abdomen part) with the trouser body 1a are smaller than the clothing pressures at the abdomen part with the conventional trousers.

In general, the acceptable limit value for clothing pressure is said to be 3.92 kPa. Compared to the limit value, the maximum clothing pressure with the trouser body 1a is 2.83 kPa. That is, none of the clothing pressures with the trouser body 1a exceeds the acceptable limit value. Accordingly, in addition to the advantageous effect in which the trouser body 1a can contribute to prevent the backache of the wearer, the trouser body 1a is able to suppress high blood pressure, an increase in pulse rate, a physiological phenomenon such as sweating, physical weariness, backache, and sense of vomiting.

Figure 23:
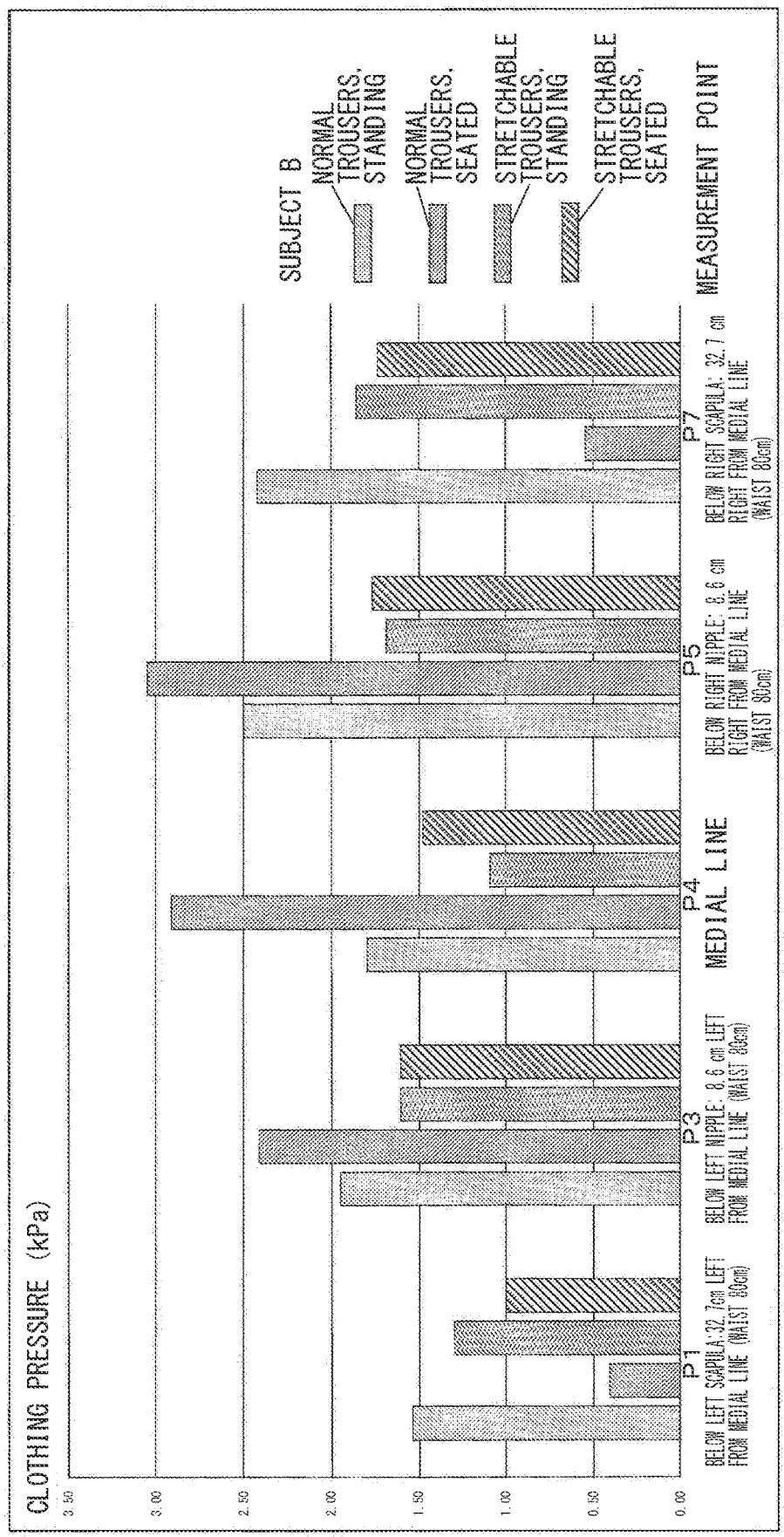
FIG. 23 is a fourth reference material showing a part of the measurement results of the clothing pressures shown in FIGS. 22A, 22B.

The fourth material in FIG. 23 is a graph showing the data of the tables (III) and (IV). The reference signs P3, P4, P5 represent the point directly below the left nipple of the subject, the point of the medal line of the subject, and the point directly below the right nipple of the subject. The bar graphs show the measured clothing pressures at each point P3 to P5. The points P3 to P5 are positioned within the area corresponding to the front surface of the stretchable cloth 15 provided at the back body part.

The clothing pressures at the above-mentioned points in the seated posture are greater than that in the standing posture, and the difference between each posture is reduced by providing the stretchable cloth 15. Further, the reference signs P1, P7 represent the point directly below the right scapula P1 and the point directly below the left scapula P7. The points P1 and P7 are positioned within the area corresponding to the back surface of the stretchable cloth 15 provided at the back body part.

The clothing pressures at these points in the seated posture are smaller than that in the standing posture, and the difference between each posture is reduced by providing the stretchable cloth 15. This means, compared to the conventional trousers, the trouser body 1a can suppress the increase in the clothing pressures at the front side of the wearer and can maintain the clothing pressures at the back side of the wearer when the wearer takes the seated posture. In other words, the trouser body 1a does not excessively press the abdomen part and can prevent the trouser body 1a from sliding down.

As described above, the trousers with the waist protection belt 1 are suitable as light-work trousers and can eliminate the gap between the rear belt part 11b on the back side of the trousers and the waist part of the wearer when the wearer is in the crouching posture. Further, the trousers 1 include the waist stretchable part 20 at the area of the back body part where the skin extends. The waist stretchable part 20 is configured to expand in accordance with the extension of the skin so as to reduce the abdominal pressure by the front belt part 11a. The waist stretchable part 20 is provided at the trousers 1 to prevent the tension at the rear belt part 11b and to reduce the abdominal pressure by the front belt part 11a when the wearer is, for example, in the seated posture. Since the waist stretchable part 20 is applied only to the required area on the waist part in which the skin extends (i.e., the width of the waist stretchable part 20 is kept minimum), it is possible to fabricate the appearance of the trousers as light-work trousers.

As described above, the extension amount of the trousers 1 is zero at a position away from the spine position by a predetermined distance in the crouching posture and in the seated posture. Rather, the skin itself on the waist part at the position away from the spine position by the predetermined distance (i.e., 13.5 cm or longer in the example of FIG. 20) shrinks. Therefore, if the stretchable cloth 15 is provided at this part, the trousers would have a bulge unnecessary in the crouching posture or the like. Such a bulge is waste of the cloth, and further may cause a hazardous situation as the bulge may get caught by a protruding object. Accordingly, it is preferable to make the width of the stretchable cloth 15 correspond to the distance between the centers of the back pockets 22, 23.

As described above, the trousers 1 according to the First Embodiment of this disclosure include the trouser body 1a, the stretchable cloth 15 provided at the area corresponding to the waist part of the trouser body 1a, and the waist protection belt 31 detachably attached to the belt cloth 10 of the trouser body.

The trousers 1 according to the First Embodiment are configured as described above. Therefore, it is possible to maintain the wearing position of the waist protection belt 31 at the desirable position even if the wearer changes his position to the crouching posture and/or to the seated posture. That is, when the wearer changes his posture to, for example, the crouching posture and the trouser body 1a is pulled downward, the stretchable cloth 15 extends appropriately to prevent the belt part 11 (belt cloth 10) and the waist protection belt 31, which is attached to the belt part 11, from sliding downward. As the belt part 11 does not slide downward, it is possible to prevent the abdomen part of the wearer from being pressed excessively.

Second Embodiment

Next, trousers with a waist protection belt 1 according to a Second Embodiment of this disclosure will be described. In the Second Embodiment, the elements identical to those of the First Embodiment are indicated by the same reference signs, and detailed description thereof will be omitted.

FIGS. 16A, 16B illustrate a waist protection belt 310 according to the Second Embodiment of this disclosure. As illustrated in FIGS. 16A, 16B, the waist protection belt 310 according to the Second Embodiment includes an attachment position adjusting part 71 at substantially the center of a belt main body 32 (to be specific, at a connection cloth 70 thereof). The attachment position adjusting part 71 is configured such that the attachment position of the waist protection belt 310 in the vertical direction with respect to a trouser body 1a is adjustable. Therefore, the wearer can detachably attach the waist protection belt 310 to the trouser body 1a through the attachment position adjusting part 71 and can appropriately adjust the position of the waist protection belt 310 in accordance with the body shape of the wearer.

To be specific, the attachment position adjusting part 71 includes at least two male fasteners or at least two female fasteners (in example illustrated in FIGS. 16A, 16B, three male fasteners 73a, 73b, 73c) arranged in a direction orthogonal to the longitudinal direction of the belt main body 32. The trouser body 1a includes, at the waist part of the belt cloth 10 of the trouser body 1a, at least one female fastener or at least one male fastener (in the example illustrated in FIGS. 8, 15, two female fasteners 40b) which engages with the fasteners provided at the attachment position adjusting part 71. Here, the attachment position adjusting part 71 is formed of the fasteners provided at the belt main body 32 (i.e., male fasteners 73a, 73b, 73c) and the fasteners provided at the trouser body 1a (i.e., female fasteners 40b, 40b).

Accordingly, the wearer can adjust the attachment position of the belt main body 32 with respect to the trouser body 1a by changing one of the male fasteners or the female fasteners provided at the belt main body 32 (i.e., male fasteners 73a, 73b, 73c) which engage with the female fasteners or the male fasteners provided at the trouser body 1a (i.e., female fasteners 40b).

Figure 17:
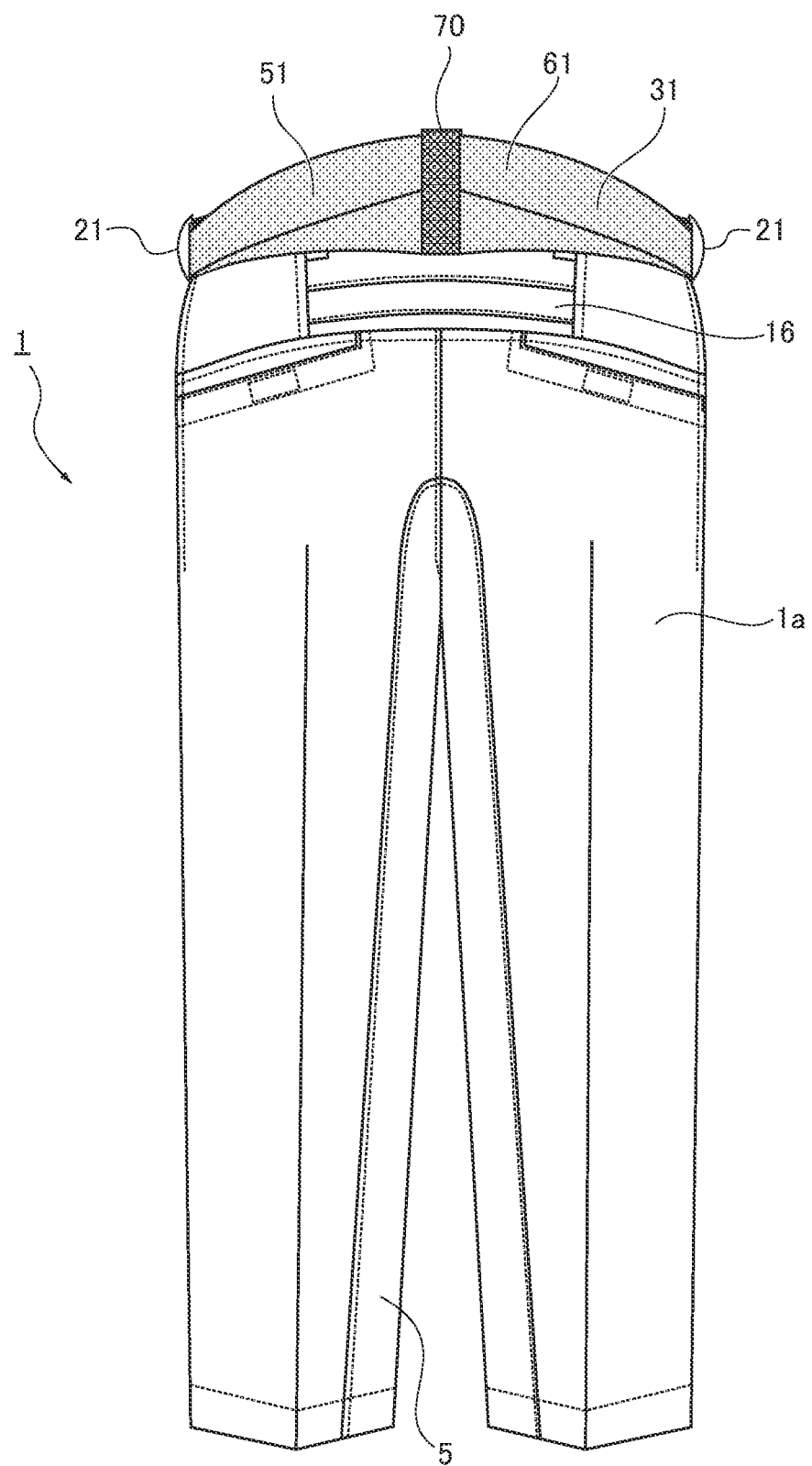
FIG. 17 is a back view illustrating trousers with the waist protection belt according to the Second Embodiment of this disclosure.

As clearly illustrated in FIGS. 3 and 17, when the male fasteners 73b, 73c on the belt main body 32 are engaged with the female fasteners 40b, 40b on the trouser body 1a, the belt main body 32 is positioned relatively lower with respect to the belt cloth 10 of the trouser body 1a (see FIG. 3). On the other hand, when the male fasteners 73a, 73b on the belt main body 32 are engaged with the female fasteners 40b, 40b on the trouser body 1a, the belt main body 32 is positioned relatively higher with respect to the belt cloth 10 of the trouser body 1a (see FIG. 17).

As described above, the trousers with the waist protection belt (1) according to the Second Embodiment can adjust the attachment position of the waist protection belt 310 using the attachment position adjusting part 71 in accordance with the body shape of the wearer. The trousers 1 can alone adjust and correct some difference in waist sizes of the wearers using the elastic members 13 provided on the sides thereof, but cannot adjust a difference in lengths above crotches of the wearers. The trousers with the waist protection belt (1) according to the Second Embodiment is, on the other hand, configured as described above such that it is possible to adjust and correct the attachment position of the waist protection belt 310 in accordance with the pelvic positions, which may differ depending on body shapes of the wearers.

In this embodiment, the male fasteners 73a, 73b, 73c provided at the belt main body 32 are arranged in the vertical direction (i.e., the direction orthogonal to the longitudinal direction of the belt main body 32) at predetermined regular intervals. Further, the female fasteners 40b, 40b, which are provided at the belt cloth 10 of the trouser body 1a and are configured to be engaged with the male fasteners 73a, 73b, 73c, are also arranged in the vertical direction at the predetermined regular intervals.

In this embodiment, the attachment position adjusting part 71 is formed of a snap tape. With this, it is possible to make the attachment position adjusting part 71 relatively thin, and thus, it is possible to reduce the sense of discomfort to the wearer when the wearer wears the trousers 1. Further, it makes easy to detachably attach the waist protection belt 310 to the trouser body 1a and to adjust the attachment position. Additionally, the engagement of the male fasteners and the female fasteners should not be disengaged easily since substantially equal tensile forces are applied to the engaged male fasteners and female fasteners from the right-side and left-side protection bands 55, 59 when the wearer wears the waist protection belt 310.

It should be noted that in the embodiment, the waist protection belt 310 may be configured to include at least one of the male fasteners 73a, 73b, 73c or at least one of the female fasteners 40b, 40b on the belt main body 32 in the direction orthogonal to the longitudinal direction of the belt main body 32, and to include at least two female fasteners 40b, 40b or at least two male fasteners on the belt cloth 10 of the trouser body 1a.

In this embodiment, the male fasteners 73a, 73b, 73c are provided at the waist protection belt 310, and the female fasteners 40b, 40b are provided at the trouser body 1a. However, the male fasteners 73a, 73b, 73c may be provided at the trouser body 1a, and the female fasteners 40b, 40b may be provided at the waist protection belt 310. Further, the configuration of the attachment position adjusting part 71 according to the Second Embodiment is not limited to the above-mentioned configuration. For example, the attachment position adjusting part 71 may be formed of touch fasteners or of fasteners having the ratchet structure.

It should be noted that the other configurations and structures of the trousers with the waist protection belt 1 in the Second Embodiment are considered to be identical or similar to those of the trousers with the waist protection belt 1 in the First Embodiment. Therefore, the functions and the advantageous effects divined by the configurations and structures of the First Embodiment are also obtained by the Second Embodiment.

The trousers with the waist protection belt according to this disclosure have been described with reference to the drawings attached hereto. However, the trousers with the waist protection belt according to this disclosure are not limited thereto.

For example, the sizes of the main belt and the like are described in detail. However, these numbers shall be handled as only examples. That is, the sizes of the waist protection belt and the trousers with the waist protection belt according to this disclosure are not limited to those numbers.

In the above-described embodiments, the left-side auxiliary belt 51 and the right-side auxiliary belt 61 are each formed in the substantially V-shape by folding the stretchable cloth. However, the configurations of the left-side auxiliary belt 51 and the right-side auxiliary belt 61 are not limited thereto. For example, each of the left-side auxiliary belt 51 and the right-side auxiliary belt 61 may directly be cut in the substantially V-shape.

In the Second Embodiment, the attachment position adjusting part 71 includes three (3) fasteners. However, the number of the fasteners is not limited to three. That is, the number of the fasteners can be modified in accordance with the required accuracy of the attachment.

The trousers with the waist protection belt according to the disclosure have been described with reference to the First and Second Embodiments. However, the detailed configurations and structures are not limited to those of the Embodiments. It should be appreciated that variations or modifications may be made in the Embodiments described by persons skilled in the art without departing from the scope of the present invention as defined by the following claims.

REFERENCE SIGNS LIST

1 Waist Protection Belt, 1a Trouser Body, 2 Front Body Part, 3 Back Body Part, 15 Stretchable Cloth, 16 Cover Cloth, 20 Waist Stretchable Part, 31 Waist Protection Belt, 33 Main Belt, 40 Detachable Part, 40a Male Fastener, 40b Female Fastener, 41 Left Connection Band, 42 First Left-Side Touch Fastener, 43 Second Left-Side Fastener, 45 Right Connection Band, 46 Right-Side Touch Fastener, 51 Left-Side Auxiliary Belt, 61 Right-Side Auxiliary Belt, 70 Connection Cloth, 71 Attachment Position Adjusting Part, 73a-73c Male Fastener

The invention claimed is:

1. Trousers with a waist protection belt comprising:
a trouser body having an inner edge of a crotch portion of a front body part sewn to an inner edge of a crotch portion of a back body part, an outer edge of the crotch portion of the front body part sewn to an outer edge of the crotch portion of the back body part, and a belt cloth sewn to an upper edge of the front body part and an upper edge of the back body part;
a waist protection belt configured to be attached to a belt part provided at an upper end of the trouser body; and
a stretchable cloth provided at a waist part of the trousers, wherein
the waist protection belt is detachably attached to an outside of the belt part via a detachable part at a position corresponding to a back of a waist part of the belt part, and
the belt part is configured to be positioned at a pelvic position of a wearer.

2. The trousers according to claim 1, wherein
the stretchable cloth is sewn to the belt part at an upper edge thereof and is sewn to a back body part of the trouser body at a lower edge thereof.

3. The trousers according to claim 1, wherein
a circumferential length of the waist protection belt is longer than a circumferential length of the belt part of the trouser body.

4. The trousers according to claim 1, further comprising a cover cloth that covers the stretchable cloth, wherein
the cover cloth is formed to have a corrugated shape by folding the cover cloth along a fold extending in a left-and-right direction.

5. The trousers according to claim 4, wherein
the cover cloth is sewn to the belt part of the trouser body at an upper edge thereof and is sewn to a back body part of the trouser body at a lower edge thereof.

6. The trousers according to claim 1, wherein
the waist protection belt is positioned to cover an anterior superior iliac spine of a wearer of the trousers from outside of the trousers.

7. The trousers according to claim 1, wherein
the waist protection belt is entirely separatably attached to the outside of the belt part via the detachable part at the position corresponding to the back of the waist part of the belt part.

8. The trousers according to claim 1, wherein
the trouser body comprises at least one belt loop, and
the waist protection belt is configured to be inserted through the at least one belt loop.

9. The trousers according to claim 1, wherein
the belt part is made of a cloth having a low stretchability.

10. The trousers according to claim 1, wherein
the stretchable cloth is configured to stretch in a vertical direction corresponding to a length direction of the trousers.

11. The trousers according to claim 1, wherein
the belt part is formed by folding the belt cloth in half and wrapping or sandwiching the upper edge of the front body part and the upper edge part of the back body part, respectively, with folded edges of the belt cloth, and sewing the upper edge parts of the front body part and the back body part with the folded edges of the belt cloth.

* * * * *